(12) United States Patent
Solberg et al.

(10) Patent No.: US 7,860,569 B2
(45) Date of Patent: Dec. 28, 2010

(54) LONG-TERM SPG STIMULATION THERAPY FOR PREVENTION OF VASCULAR DEMENTIA

(75) Inventors: Yoram Solberg, Hertzeliya (IL); Hernan Altman, Haifa (IL)

(73) Assignee: Brainsgate, Ltd., Caesarea South Industrial Park (IL)

( * ) Notice: Subject to any disclaimer, the term of this patent is extended or adjusted under 35 U.S.C. 154(b) by 31 days.

(21) Appl. No.: 11/874,529

(22) Filed: Oct. 18, 2007

(65) Prior Publication Data
US 2009/0105783 A1    Apr. 23, 2009

(51) Int. Cl.
*A61N 1/18* (2006.01)
(52) U.S. Cl. .............................. 607/45; 607/2
(58) Field of Classification Search ...................... 607/1, 607/2, 45, 46, 48, 118; 600/26
See application file for complete search history.

(56) References Cited

U.S. PATENT DOCUMENTS

| | | | |
|---|---|---|---|
| 4,666,829 A | 5/1987 | Glenner et al. |
| 4,866,042 A | 9/1989 | Neuwelt |
| 4,874,694 A | 10/1989 | Gandy et al. |
| 4,886,493 A | 12/1989 | Yee |
| 4,979,511 A | 12/1990 | Terry, Jr. et al. |
| 5,011,472 A | 4/1991 | Aebischer et al. |
| 5,031,618 A | 7/1991 | Mullett |
| 5,059,415 A | 10/1991 | Neuwelt |
| 5,154,172 A | 10/1992 | Terry, Jr. et al. |
| 5,179,950 A | 1/1993 | Stanislaw |
| 5,186,170 A | 2/1993 | Varrichio et al. |
| 5,188,104 A | 2/1993 | Wernicke et al. |
| 5,205,285 A | 4/1993 | Baker, Jr. |
| 5,215,086 A | 6/1993 | Terry, Jr. et al. |

(Continued)

FOREIGN PATENT DOCUMENTS

EP    1 559 369 A1    8/2005

(Continued)

OTHER PUBLICATIONS

ADEAR Center. Multi-Infarct Dementia Fact Sheet. US Department of Health, 2003.*

(Continued)

*Primary Examiner*—Carl H Layno
*Assistant Examiner*—Pamela M Bays
(74) *Attorney, Agent, or Firm*—RatnerPrestia

(57) ABSTRACT

A method is provided that includes identifying that a subject is at risk of suffering from vascular dementia (VaD). Responsively to the identifying, a risk of development of the VaD is reduced by applying electrical stimulation to a site of the subject selected from the group consisting of: a sphenopalatine ganglion (SPG), a greater palatine nerve, a lesser palatine nerve, a sphenopalatine nerve, a communicating branch between a maxillary nerve and an SPG, an otic ganglion, an afferent fiber going into the otic ganglion, an efferent fiber going out of the otic ganglion, an infraorbital nerve, a vidian nerve, a greater superficial petrosal nerve, and a lesser deep petrosal nerve; and configuring the stimulation to induce at least one neuroprotective occurrence selected from the group consisting of: an increase in cerebral blood flow of the subject, and a release of one or more neuroprotective substances. Other embodiments are also described.

13 Claims, 8 Drawing Sheets

U.S. PATENT DOCUMENTS

| | | |
|---|---|---|
| 5,215,089 A | 6/1993 | Baker, Jr. |
| 5,222,494 A | 6/1993 | Baker, Jr. |
| 5,223,254 A | 6/1993 | Paradiso et al. |
| 5,231,988 A | 8/1993 | Wernicke et al. |
| 5,235,980 A | 8/1993 | Varrichio et al. |
| 5,237,991 A | 8/1993 | Baker, Jr. et al. |
| 5,251,634 A | 10/1993 | Weinberg |
| 5,263,480 A | 11/1993 | Wernicke et al. |
| 5,268,164 A | 12/1993 | Kozarich et al. |
| 5,269,303 A | 12/1993 | Wernicke et al. |
| 5,299,569 A | 4/1994 | Wernicke et al. |
| 5,304,206 A | 4/1994 | Baker, Jr. et al. |
| 5,304,632 A | 4/1994 | Vaudry et al. |
| 5,330,515 A | 7/1994 | Rutecki et al. |
| 5,335,657 A | 8/1994 | Terry, Jr. et al. |
| 5,351,394 A | 10/1994 | Weinberg |
| 5,531,778 A | 7/1996 | Maschino et al. |
| 5,540,730 A | 7/1996 | Terry, Jr. et al. |
| 5,540,734 A | 7/1996 | Zabara |
| 5,571,150 A | 11/1996 | Wernicke et al. |
| 5,639,853 A | 6/1997 | Paradiso et al. |
| 5,707,400 A | 1/1998 | Terry, Jr. et al. |
| 5,725,471 A | 3/1998 | Davey et al. |
| 5,752,515 A | 5/1998 | Jolesz et al. |
| 5,756,071 A | 5/1998 | Mattern et al. |
| 5,792,100 A | 8/1998 | Shantha |
| 5,830,670 A | 11/1998 | De la Monte et al. |
| 5,833,988 A | 11/1998 | Friden |
| 5,849,600 A | 12/1998 | Nixon et al. |
| 5,855,907 A | 1/1999 | Peyman |
| 5,928,272 A | 7/1999 | Adkins et al. |
| 5,938,689 A | 8/1999 | Fischell et al. |
| 5,938,690 A | 8/1999 | Law et al. |
| 5,981,194 A | 11/1999 | Jefferies et al. |
| 5,985,581 A | 11/1999 | Nixon et al. |
| 6,001,331 A | 12/1999 | Caprathe et al. |
| 6,005,004 A | 12/1999 | Katz et al. |
| 6,006,124 A | 12/1999 | Fischell et al. |
| 6,016,449 A | 1/2000 | Fischell et al. |
| 6,061,593 A | 5/2000 | Fischell et al. |
| 6,066,163 A | 5/2000 | John |
| 6,071,705 A | 6/2000 | Wands et al. |
| 6,086,525 A | 7/2000 | Davey et al. |
| 6,087,118 A | 7/2000 | Aronson et al. |
| 6,114,175 A | 9/2000 | Klunk et al. |
| 6,117,454 A | 9/2000 | Kreuter et al. |
| 6,128,538 A | 10/2000 | Fischell et al. |
| 6,130,048 A | 10/2000 | Nixon |
| 6,132,977 A | 10/2000 | Thompson et al. |
| 6,134,474 A | 10/2000 | Fischell et al. |
| 6,161,045 A | 12/2000 | Fischell et al. |
| 6,200,768 B1 | 3/2001 | Mandelkow et al. |
| 6,210,895 B1 | 4/2001 | Schipper et al. |
| 6,211,235 B1 | 4/2001 | Wu et al. |
| 6,230,049 B1 | 5/2001 | Fischell et al. |
| 6,232,326 B1 | 5/2001 | Nelson |
| 6,238,892 B1 | 5/2001 | Mercken et al. |
| 6,277,841 B1 | 8/2001 | Rajagopalan et al. |
| 6,287,793 B1 | 9/2001 | Schenk et al. |
| 6,322,494 B1 | 11/2001 | Bullivant et al. |
| 6,325,475 B1 | 12/2001 | Hayes et al. |
| 6,329,531 B1 | 12/2001 | Turner et al. |
| 6,338,715 B1 | 1/2002 | Hayes et al. |
| 6,353,754 B1 | 3/2002 | Fischell et al. |
| 6,354,299 B1 | 3/2002 | Fischell et al. |
| 6,358,681 B2 | 3/2002 | Ginsberg et al. |
| 6,360,122 B1 | 3/2002 | Fischell et al. |
| 6,405,079 B1 | 6/2002 | Ansarinia |
| 6,410,046 B1 | 6/2002 | Lerner |
| 6,415,184 B1 | 7/2002 | Ishikawa et al. |
| 6,427,086 B1 | 7/2002 | Fischell et al. |
| 6,432,986 B2 | 8/2002 | Levin |
| 6,459,936 B2 | 10/2002 | Fischell et al. |
| 6,466,822 B1 | 10/2002 | Pless |
| 6,473,639 B1 | 10/2002 | Fischell et al. |
| 6,473,644 B1 | 10/2002 | Terry, Jr. et al. |
| 6,480,743 B1 | 11/2002 | Kirkpatrick et al. |
| 6,491,940 B1 | 12/2002 | Levin |
| 6,526,318 B1 | 2/2003 | Ansarinia |
| 6,529,774 B1 | 3/2003 | Greene |
| 6,531,454 B1 | 3/2003 | Leary et al. |
| 6,587,719 B1 | 7/2003 | Barrett et al. |
| 6,587,724 B2 | 7/2003 | Mann |
| 6,591,137 B1 | 7/2003 | Fischell et al. |
| 6,591,138 B1 | 7/2003 | Fischell et al. |
| 6,597,953 B2 | 7/2003 | Boling |
| 6,597,954 B1 | 7/2003 | Fischell et al. |
| 6,606,521 B2 | 8/2003 | Paspa et al. |
| 6,609,025 B2 | 8/2003 | Barrett et al. |
| 6,609,032 B1 | 8/2003 | Woods et al. |
| 6,609,956 B2 | 8/2003 | Margaria |
| 6,618,623 B1 | 9/2003 | Pless et al. |
| 6,622,038 B2 | 9/2003 | Barrett et al. |
| 6,622,041 B2 | 9/2003 | Terry et al. |
| 6,622,047 B2 | 9/2003 | Barrett et al. |
| 6,647,296 B2 | 11/2003 | Fischell et al. |
| 6,662,035 B2 | 12/2003 | Sochor |
| 6,678,553 B2 | 1/2004 | Lerner et al. |
| 6,690,974 B2 | 2/2004 | Archer et al. |
| 6,735,474 B1 | 5/2004 | Loeb et al. |
| 6,810,285 B2 | 10/2004 | Pless et al. |
| 6,811,788 B2 | 11/2004 | Yu |
| 6,853,858 B2 | 2/2005 | Shalev |
| 6,905,827 B2 | 6/2005 | Wohlgemuth et al. |
| 7,120,489 B2 * | 10/2006 | Shalev et al. .................. 607/2 |
| 2001/0004644 A1 | 6/2001 | Levin |
| 2001/0014670 A1 | 8/2001 | Balin et al. |
| 2001/0018191 A1 | 8/2001 | Mercken et al. |
| 2001/0020097 A1 | 9/2001 | Audia et al. |
| 2001/0026916 A1 | 10/2001 | Ginsberg et al. |
| 2001/0027309 A1 | 10/2001 | Elsberry |
| 2001/0044126 A1 | 11/2001 | Holtzman et al. |
| 2001/0047014 A1 | 11/2001 | Alanine et al. |
| 2001/0051633 A1 | 12/2001 | Bigge et al. |
| 2002/0002270 A1 | 1/2002 | Zinkowski et al. |
| 2002/0006627 A1 | 1/2002 | Reitz et al. |
| 2002/0009445 A1 | 1/2002 | Du et al. |
| 2002/0019016 A1 | 2/2002 | Vanmechelen et al. |
| 2002/0019412 A1 | 2/2002 | Andersen et al. |
| 2002/0019519 A1 | 2/2002 | Bingham et al. |
| 2002/0022242 A1 | 2/2002 | Small et al. |
| 2002/0022593 A1 | 2/2002 | Yue |
| 2002/0022621 A1 | 2/2002 | Chaturvedula et al. |
| 2002/0022650 A1 | 2/2002 | Posmantur et al. |
| 2002/0025955 A1 | 2/2002 | Han et al. |
| 2002/0026652 A1 | 2/2002 | Allen et al. |
| 2002/0028462 A1 | 3/2002 | Tanzi et al. |
| 2002/0028834 A1 | 3/2002 | Villalobos et al. |
| 2002/0035145 A1 | 3/2002 | Tsai et al. |
| 2002/0040032 A1 | 4/2002 | Glasky et al. |
| 2002/0040052 A1 | 4/2002 | Ito et al. |
| 2002/0042121 A1 | 4/2002 | Riesner et al. |
| 2002/0042420 A1 | 4/2002 | Briem et al. |
| 2002/0044919 A1 | 4/2002 | Yu |
| 2002/0052311 A1 | 5/2002 | Solomon et al. |
| 2002/0055501 A1 | 5/2002 | Olson et al. |
| 2002/0066959 A1 | 6/2002 | Joshi |
| 2002/0068080 A1 | 6/2002 | Lerner |
| 2002/0082583 A1 | 6/2002 | Lerner |
| 2002/0099412 A1 | 7/2002 | Fischell et al. |
| 2002/0099417 A1 | 7/2002 | Naritoku et al. |
| 2002/0123678 A1 | 9/2002 | Lerner et al. |
| 2002/0133841 A1 | 9/2002 | Leviten |
| 2002/0169307 A1 | 11/2002 | Klein |

| Publication No. | Date | Inventor |
|---|---|---|
| 2002/0169485 A1 | 11/2002 | Pless et al. |
| 2002/0183683 A1 | 12/2002 | Lerner |
| 2003/0005473 A1 | 1/2003 | Brennan et al. |
| 2003/0005477 A1 | 1/2003 | Leviten |
| 2003/0013136 A1 | 1/2003 | Balser et al. |
| 2003/0014772 A1 | 1/2003 | Allen |
| 2003/0018988 A1 | 1/2003 | Allen et al. |
| 2003/0018989 A1 | 1/2003 | Brennan et al. |
| 2003/0036781 A1 | 2/2003 | Nuttin et al. |
| 2003/0050527 A1 | 3/2003 | Fox et al. |
| 2003/0051268 A1 | 3/2003 | Allen |
| 2003/0056238 A1 | 3/2003 | Wisotzkey |
| 2003/0073917 A1 | 4/2003 | Echauz et al. |
| 2003/0074033 A1 | 4/2003 | Pless et al. |
| 2003/0079742 A1 | 5/2003 | Giroux |
| 2003/0106083 A1 | 6/2003 | Allen |
| 2003/0131367 A1 | 7/2003 | Guenther et al. |
| 2003/0133877 A1 | 7/2003 | Levin |
| 2003/0144711 A1 | 7/2003 | Pless et al. |
| 2003/0149457 A1 | 8/2003 | Tcheng et al. |
| 2003/0166099 A1 | 9/2003 | Sabbadini et al. |
| 2003/0166279 A1 | 9/2003 | Sabbadini et al. |
| 2003/0172390 A1 | 9/2003 | Wisotzkey et al. |
| 2003/0176892 A1 | 9/2003 | Shalev |
| 2003/0176898 A1 | 9/2003 | Gross et al. |
| 2003/0190601 A1 | 10/2003 | Sabbadini et al. |
| 2003/0190683 A1 | 10/2003 | Sabbadini et al. |
| 2003/0190749 A1 | 10/2003 | Surber et al. |
| 2003/0191426 A1 | 10/2003 | Lerner et al. |
| 2003/0194714 A1 | 10/2003 | Sabbadini et al. |
| 2003/0195588 A1 | 10/2003 | Fischell et al. |
| 2003/0195602 A1 | 10/2003 | Boling |
| 2003/0198995 A1 | 10/2003 | Sabbadini et al. |
| 2003/0198996 A1 | 10/2003 | Surber et al. |
| 2003/0199005 A1 | 10/2003 | Sabbadini et al. |
| 2003/0199088 A1 | 10/2003 | Sabbadini et al. |
| 2003/0199089 A1 | 10/2003 | Surber et al. |
| 2003/0202937 A1 | 10/2003 | Sabbadini et al. |
| 2003/0203411 A1 | 10/2003 | Sabbadini et al. |
| 2003/0203481 A1 | 10/2003 | Surber et al. |
| 2003/0207833 A1 | 11/2003 | Berkley et al. |
| 2003/0211086 A1 | 11/2003 | Berkley et al. |
| 2003/0211599 A1 | 11/2003 | Sabbadini et al. |
| 2003/0219408 A1 | 11/2003 | Sabbadini et al. |
| 2003/0219888 A1 | 11/2003 | Segall et al. |
| 2003/0224369 A1 | 12/2003 | Surber et al. |
| 2003/0224444 A1 | 12/2003 | Sabbadini et al. |
| 2003/0232335 A1 | 12/2003 | Surber et al. |
| 2004/0015068 A1 | 1/2004 | Shalev et al. |
| 2004/0033491 A1 | 2/2004 | Alsobrook et al. |
| 2004/0054297 A1 | 3/2004 | Wingeier et al. |
| 2004/0133248 A1 | 7/2004 | Frei et al. |
| 2004/0136950 A1 | 7/2004 | Ni et al. |
| 2004/0136951 A1 | 7/2004 | Ni et al. |
| 2004/0153129 A1 | 8/2004 | Pless et al. |
| 2004/0210269 A1 | 10/2004 | Shalev et al. |
| 2004/0220644 A1 | 11/2004 | Shalev et al. |
| 2005/0020519 A1 | 1/2005 | Albiston et al. |
| 2005/0054939 A1 | 3/2005 | Ben-Ari et al. |
| 2005/0074506 A1 | 4/2005 | Natan et al. |
| 2005/0112090 A9 | 5/2005 | Ni et al. |
| 2005/0118187 A1 | 6/2005 | Yu |
| 2005/0137646 A1 | 6/2005 | Wallace et al. |
| 2005/0137647 A1 | 6/2005 | Wallace et al. |
| 2005/0159790 A1* | 7/2005 | Shalev .................. 607/45 |
| 2005/0177514 A1 | 8/2005 | Sasselli |
| 2005/0266099 A1 | 12/2005 | Shalev |
| 2006/0020299 A1 | 1/2006 | Shalev |
| 2006/0195169 A1 | 8/2006 | Gross |
| 2006/0287677 A1 | 12/2006 | Shalev |
| 2006/0293723 A1* | 12/2006 | Whitehurst et al. ........... 607/48 |
| 2007/0083245 A1 | 4/2007 | Lamensdorf et al. |

FOREIGN PATENT DOCUMENTS

| | | |
|---|---|---|
| JP | 08-229141 | 9/1996 |
| WO | WO 93/09841 | 5/1993 |
| WO | WO 93/25271 | 12/1993 |
| WO | WO 97/18855 | 5/1997 |
| WO | WO 99/03473 | 1/1999 |
| WO | WO 00/44432 | 8/2000 |
| WO | WO 00/73343 A2 | 12/2000 |
| WO | WO 01/43733 A2 | 6/2001 |
| WO | WO 01/85094 A2 | 11/2001 |
| WO | WO 01/97905 A1 | 12/2001 |
| WO | WO 02/32504 A2 | 4/2002 |
| WO | WO 02/068029 A2 | 9/2002 |
| WO | WO 02/068031 A2 | 9/2002 |
| WO | WO 02/094191 A2 | 11/2002 |
| WO | WO 03/000310 A2 | 1/2003 |
| WO | WO 03/020350 A1 | 3/2003 |
| WO | WO 03/063959 A1 | 8/2003 |
| WO | WO 03/084591 A1 | 10/2003 |
| WO | WO 03/090599 A2 | 11/2003 |
| WO | WO 03/105658 A2 | 12/2003 |
| WO | WO 2004/010923 A2 | 2/2004 |
| WO | WO 2004/043217 A2 | 5/2004 |
| WO | WO 2004/043218 A2 | 5/2004 |
| WO | WO 2004/043334 A2 | 5/2004 |
| WO | WO 2004/044947 A2 | 5/2004 |
| WO | WO 2004/045242 A2 | 5/2004 |
| WO | WO 2004/064918 A1 | 8/2004 |
| WO | WO 2005/030025 A2 | 4/2005 |
| WO | WO 2005/030118 A2 | 4/2005 |
| WO | WO 2006/021957 A2 | 3/2006 |

OTHER PUBLICATIONS

Lojkowska, W. et al."The Effect ofCholinesterase Inhibitors on the Regional Blood Flow in Patients with Alzheimer's disease and Vascular Dementia." Journel of the Neurological Sciences 216 (2003): 119-26.*

Japanese Office Action dated Sep. 16, 2008, which issued during the prosecution of Applicant's Japanese Patent U.S. Appl. No. 2001-581749.

Suzuki et al.; "Effect on cortical blood flow of electrical stimulation of trigeminal cerebrovascular nerve fibres in the rat"; Acta Physio Scand 1990, 138, 307-315.

Major et al.; "Odorants Presented to the Rat Nasal Cavity Increase Cortical Blood Flow"; Chem. Senses 24: 665-669, 1999.

Fusco et al.; "'Capsaicin-Sensitive' Sensory Neurons in Cluster Headache: Pathophysiological Aspects and Therapeutic Indication"; Headache, 34, 132-137, 1994.

Lambert et al.; "Decreased carotid arterial resistance in cats in response to trigeminal stimulation"; Journal of Neurosurgery, 61, 307-315, 1984.

Silver; "Neural and Pharmacological Basis for Nasal Irritation"; Annals New York Academy of Sciences, 152-163, 1992.

Sikic et al.; "Modulation and prevention of multidrug resistance by inhibitors of P-glycoprotein"; Cancer Chemother Pharmacol (1997) 40 (Suppl.): S13-S-19.

Fu et al.; "Improved bioavailability of orally administered drugs by Chinese herbal enhancers through modulation of P-glycoprotein"; ASHP 39th Midyear Clinical Meeting and Exhibits, Dec. 5-9, 2004, Orlando, FL, Presentation Abstracts.

Delepine et al.; "Plasma Protein Extravasation Induced in the Rat Dura Mater by Stimulation of the Parasympathetic Sphenopalatine Ganglion"; Experimental Neurology, 147, 389-400, 1997.

Hara et al.; "Parasympathetic Cerebrovascular Innervation: An Anterograde Tracing from the Spenopalatine Ganglion in the Rat"; Neurosurgery, vol. 32, No. 5, May 1993, 822-827.

Ruskell; "The orbital branches of the pterygopalatine ganglion and their relationship with internal carotid nerve branches in primates"; J. Anat. 1970, 106, 2, 323-339.

Kroll et al; "Outwitting the Blood-Brain Barrier for Therapeutic Purposes: Osmotic Opening and Other Means"; Neurosurgery, vol. 42, No. 5, May 1998, 1083-1100.

Sanders et al; "Efficacy of spenopalatine ganglion blockade in 66 patients suffering from cluster headache: a 12- to 70-month follow-up evaluation"; J. Neurosurg., vol. 87, Dec. 1997, 876-880.

Suzuki et al; "Selective Electrical Stimulations of Postganglionic Cerebrovascular Parasympathetic Nerve Fibers Originating from the Sphenopalatine Ganglion Enhances Cortical Blood Flow in the Rat"; Journal of Cerebral Blood Flow and Metabolism, 10:383-391, 1990.

Samad et al.; "Interluken-1beta-mediated induction of Cox-2 in the CNS contributes to inflammatory pain hypersensitivity"; Nature, vol. 410, Mar. 22, 2001, 471-475.

Van De Waterbeemd et al.; "Estimation of Blood-Brain Barrier Crossing of Drugs Using Molecular Size and Shape, and H-Bonding Descriptors"; Journal of Drug Targeting, 6, 151-165, 1998.

Young; "Electrical stimulation of the trigeminal nerve root for the treatment of chronic facial pain"; J Neurosurg 83:72-78, 1995.

Suzuki et al.; "Origins and Pathways of Cerebrovascular Vasoactive Intestinal Polypeptide-Positive Nerves in Rat"; Journal of Cerebral Blood Flow and Metabolism, vol. 8 No. 5, 697-712, 1988.

U.S. Appl. No. 60/364,451.
U.S. Appl. No. 60/368,657.
U.S. Appl. No. 10/522,615.
U.S. Appl. No. 60/426,181.
U.S. Appl. No. 10/525,025.
U.S. Appl. No. 60/448,807.
U.S. Appl. No. 60/461,232.
U.S. Appl. No. 60/506,165.
U.S. Appl. No. 60/604,037.

Hotta H et al., in an article entitled, "Effects of stimulating the nucleus basalis of Meynert on blood flow and delayed neuronal death following transient ischemia in rat cerebral cortes," Jap J Phys 52:383-393 (2002).

Segher O et al., in an article entitled, "Spinal cord stimulation reducing infract volume in model of focal cerebral ischemia in rats," J Neurosurg 99(1):131-137 (2003).

Goadsby PJ et al., "Effect of stimulation of trigeminal ganglion on regional cerebral blood flow in cats," Am J Physiol 22:R270-R274 (1987).

Matsui T et al., in an article entitled, "The effects of cervical spinal cord stimulation (cSCS) on experimental stroke," Pacing Clin Electrophysiol 12(4 Pt 2):726-32 (1989).

Suzuki N et al., "Trigeminal fibre collaterals storing substance P and calcitonin gene-related peptide associate with ganglion cells containing choline acetyltransferase and vasoactive intestinal polypeptide in the sphenopalatine ganglion of the rat. An axon reflex modulating parasympathetic ganglionic activity?" Neuroscience 30:595-604 (1989).

Walters BB et al., "Cerebrovascular projections from the sphenopalatine and otic ganglia to the middle cerebral artery of the cat," Stroke 17:488-494 (1986).

Branston NM, "The physiology of the cerebrovascular parasympathetic innervation," British Journal of Neurosurgery 9:319-329 (1995).

Branston NM et al., "Contribution of cerebrovascular parasympathetic and sensory innervation to the short-term control of blood flow in rat cerebral cortex," J Cereb Blood Flow Metab 15(3) 525-31 (1995).

Sun Y et al., "Neuronal nitric oxide synthase and ischemia-induced neurogenesis," J Cereb Blood Flow Metab 25(4):485-92 (2005).

Zhang F et al., "Nitric oxide donors increase blood flow and reduce brain damage in focal ischemia: evidence that nitric oxide is beneficial in the early stages of cerebral ischemia," J Cereb Blood Flow Metab 14(2):217-26 (1994).

Schmid-Elsaesser R et al., "A critical reevaluation of the intraluminal thread model of focal cerebral ischemia. Evidence of inadvertent premature reperfusion and subarachnoid hemorrhage in rats by laser-Doppler flowmetry," Stroke 29:2162-2170 (1998).

Jolliet-Riant P, Tillement JP, "Drug transfer across the blood-brain barrier and improvement of brain delivery," Fundam. Clin. Pharmacol., 13, 16-25 (1999).

Syelaz J, Hara H, Pinard E, Mraovitch S, MacKenzie ET, Edvinsson L, "Effects of stimulation of the sphenopalatine ganglion on cortical blood flow in the rat," Journal of Cerebral Blood Flow and Metabolism, 8, 875-878 (1988).

Toda N et al., "Cerebral vasodilation induced by stimulation of the pterygopalatine ganglion and greater petrosal nerve in anesthetized monkeys," Neuroscience 96(2):393-398 (2000).

Varghese et al., "Endoscopic transnasal neurolytic sphenopalatine ganglion block for head and neck cancer pain," J Laryngol Otol 115(5):385-7 (2001).

Roman GC, "Cholinergic dysfunction in vascular dementia," Curr Psychiatry Rep 7(1):18-26 (2005).

Van Gijn J et al., "Subarachnoid haemorrhage: diagnosis, causes and management," Brain 124:249-278 (2001).

Davis SM et al., "Advances in penumbra imaging with MR," Cerebrovasc Dis 17 Suppl 3:23-7 (2004).

Zausinger VS et al., "Neurological impairment in rats after transient middle cerebral artery occlusion: a comparative study under various treatment paradigms," Brain Research 863(1-2):94-105 (2000).

Phan TG et al., "Salvaging the ischaemic penumbra: more than just reperfusion?" Clin Exp Pharmacol Physiol 29(1-2):1-10 (2002).

Zhang ZG et el., "VEGF enhances angiogenesis and promotes blood-brain barrier leakage in the ischemic brain," J Clin Invest 106:829-838 (2000).

Kawamata T et al., "Intracisternal basic fibroblast growth factor (bFGF) enhances behavioral recovery following focal cerebral infarction in the rat," J Cereb Blood Flow Metab 16:542-547 (1996).

Ziche M et al., "Nitric oxide and angiogenesis," J Neurooncol 50:139-148 (2000).

Zhang R et al., "A nitric oxide donor induces neurogenesis and reduces functional deficits after stroke in rats," Ann Neurol 50:602-611 (2001).

de la Torre JC, "Vascular basis of Alzheimer's pathogenesis," Ann NY Acad Sci 977:196-215 (2002).

Hunter AJ et al., "To what extent have functional studies of ischemia in animals been useful in the assessment of potential neuroprotective agents?" Trends Pharmacol Sci 19:59-66 (1998).

Kanner AA et al., "Serum S100beta: a noninvasive marker of blood-brain barrier function and brain lesions," Cancer 97(11):2806-13 (2003).

Tony JFL, "Nitric oxide and the cerebral vascular function," J Biomed Sci 7:16-26 (2000).

Sandgren K et al., "Vasoactive intestinal peptide and nitric oxide promote survival of adult rat myenteric neurons in culture," J Neurosci Res 72(5):595-602 (2003).

Laude K et al., "NO produced by endothelial NO synthase is a mediator of delayed preconditioning-induced endothelial protection," Am J Physiol Heart Circ Physiol 284(6):H2053-60 (2003) (Epub Jan. 9, 2003).

Khan M et al., "S-Nitrosoglutathione reduces inflammation and protects brain against focal cerebral ischemia in a rat model of experimental stroke," J Cereb Blood Flow Metab 25(2):177-92 (2005).

Pluta RM, "Delayed cerebral vasospasm and nitric oxide: review, new hypothesis, and proposed treatment," Pharmacol Ther 105(1):23-56 (2005).

Reis et al., "Electrical Stimulation of Cerebellar Fastigial Nucleus Reduces Ischemic Infarction Elicited by Middle Cerebral Artery Occlusion in Rat," Journal of Cerebral Blood Flow and Metabolism, 11:810-818, 1991.

Nollet et al., "Transcranial magnetic stimulation: review of the technique, basic principles and applications," The Veterinary Journal, 166 (2003) 28-42.

Devoghel JC, "Cluster headache and spenopalatine block," Acta Anaesthesiol Belg., 1981, 32, 101-107, an abstract.

Office Action dated Jun. 27, 2008, which issued during the prosecution of Applicants' U.S. Appl. No. 10/518,322.

* cited by examiner

LONG-TERM SPG STIMULATION THERAPY FOR PREVENTION OF VASCULAR DEMENTIA

FIELD OF THE INVENTION

The present invention relates generally to medical procedures and devices. More specifically, the invention relates to the use of stimulation for treating medical conditions.

BACKGROUND OF THE INVENTION

A large portion of the elderly population suffers from a chronic decline in blood supply to the brain. In most people this decline leads to the gradual formation of brain atrophy, accompanied by a slow decline in cognitive functions which characterizes the normal elderly state. "Minimal cognitive impairment" is characterized by a certain threshold of tissue loss and cognitive malfunction, while "dementia" is characterized by a further decline that crosses a pathological threshold. Dementia patients suffer from varying degrees of memory loss, cognitive dysfunctions, and behavioral disturbances, leading in the terminally ill patient to a fully dependent state with profound personal dysfunction, as well as socioeconomic burden on the patient's family and community.

Vascular dementia (VaD) is secondary in prevalence to Alzheimer's disease (Roman G C et al. (1991); all references cited hereinbelow). The prevalence of VaD increases with age and ranges from 1.0% at 55 years, 4.2% at 70 years, increasing to up to 6.7% at 85-90 years (Lobo A et al., Ott A et al., White L et al.). Based on an estimated overall prevalence of 2.7% in people 65 or older (Lobo A et al., Rocca W A et al.), there are expected to be about 2 million VaD patients in 2030 in the United States alone (Bachman D L et al.).

The cost for caring for this growing number of demented patients is increasing dramatically. The disorder represents an immense burden not only to patients, but also to their caregivers, the health care system, and to society at large. Recently, Sicras A et al. found that the overall yearly cost of care per VaD patient in Spain is about 22,000 Euro.

VaD is a heterogeneous disease entity characterized by several different vascular mechanisms and pathological changes in the brain. Subcortical VaD, which is responsible for about two-thirds of all progressive VaD cases (Chui H, Roman G C et al. (1993), is a relatively homogeneous subtype of the disease, incorporating small vessel arteriosclerosis as a primary vascular pathological etiology, lacunar infarcts and white matter lesions (leukoaraiosis) as primary types of brain lesions, and subcortical areas as the primary location of the disease (Erkinjuntti et al.). The arteriosclerotic process leads to a progressive narrowing of the lumen of subcortical small blood vessels with a consequent long lasting reduction of cerebral blood flow (CBF) and chronic ischemia of the surrounding parenchyma (Pantoni L et al.). This diffuse chronic ischemia of the subcortical white matter results in rarefaction of the nerve fibers' myelin sheaths and to a reactive gliosis (Brun A et al.), reduced brain metabolism (Capizzano A A et al.) and loss of function, a phenomena called leukoaraiosis, which is best viewed as white matter hyperintensities in T2/Flair MRI (Hatchinski V C et al.).

It is now well accepted that hypoperfusion plays a crucial role in the pathogenesis of leukoaraiosis and the consequent decline in cognitive functions (Meyer J S et al., Mortel K F et al., Yoshikawa T et al., Zimny A et al.). Markus H S et al. and O'Sullivan M et al. demonstrated using perfusion based MRI that leukoaraiotic white matter lesions are characterized by reduced CBF. Similar results have been obtained with positron emission tomography (PET) (Meyer E et al.). Moreover, there is a clear correlation between the extent and the severity of the subcortical leukoaraiosis and the underlying degree of cerebral hypoperfusion (Kawamura J et al.).

Recent large scale prospective studies (for a review see Schmidt R et al. (2007)) indicated that leukoaraiosis progresses over time and that its extent at baseline is an important predictor for the subsequent rate of lesion progression (Enzinger C et al., Schmidt R et al. (2003)). For instance, individuals with early confluent and confluent leukoaraiotic changes tend to progress rapidly. Moreover, it is now well recognized that the progression of leukoaraiosis closely relates to the rate of cognitive decline (Garde E et al., Schmidt R et al. (2005)), and especially the decline in executive functions (Bombois S et al., Markus H S et al.), a hallmark of VaD cognitive impairment.

Thus, in subcortical VaD there is a clear pathophysiological cascade in which arteriosclerosis of the subcortical small vessels leads to progressive hypoperfusion and long lasting ischemia, which eventually leads to white matter damage, expanding leukoaraiosis, and gradual cognitive decline. A therapy aimed at treating the underlying hypoperfusion state is expected to slow down, stop, and even improve the leukoaraiotic state and the patient's cognitive status. Indeed, in a small (n=8) group of VaD patients treated for 12 months with Rivastigmine, an acetylcholinesterase inhibitor, Lojkowska et al. demonstrated an increase in regional CBF (especially in the brain frontal regions) accompanied with stabilization of the cognitive function in comparison to non-treated control patients, in whom decreases in both CBF and scores on neuropsychological tests were observed.

US Patent Application Publication 2007/0083245 to Lamensdorf et al., which is assigned to the assignee of the present application and is incorporated herein by reference, describes apparatus for treatment, including one or more electrodes, configured to be applied to a site of a subject, and adverse cerebrovascular condition treatment functionality. The functionality comprises a control unit configured to drive the one or more electrodes to apply electrical stimulation to the site during a plurality of stimulation periods which includes at least first and last stimulation periods, set an inter-period interval between initiation of the first stimulation period and initiation of the last stimulation period to be at least 24 hours, and configure the stimulation during the first and last stimulation periods to induce at least one neuroprotective occurrence selected from the group consisting of: an increase in cerebral blood flow (CBF) of the subject, and a release of one or more neuroprotective substances. The site is selected from the group consisting of: a sphenopalatine ganglion (SPG), a greater palatine nerve, a lesser palatine nerve, a sphenopalatine nerve, a communicating branch between a maxillary nerve and an SPG, an otic ganglion, an afferent fiber going into the otic ganglion, an efferent fiber going out of the otic ganglion, an infraorbital nerve, a vidian nerve, a greater superficial petrosal nerve, and a lesser deep petrosal nerve.

The '245 publication describes an in vivo experiment assessing the effect of long-term rehabilitative SPG stimulation, measured in accordance with an embodiment of the present invention. A rat tMCAO model of stroke was used to evaluate the benefits, including neuromuscular, motility, cognitive, somatosensory, somatomotor, infarct volume benefits, of rehabilitative SPG stimulation using the techniques described therein. The stimulation was applied for seven consecutive days beginning at 24 hours after reperfusion in the tMCAO model. In summary, in the experiment, SPG stimulation initiated 24 hours after tMCAO had advantageous results for all five parameter groups evaluated. In addition, SPG stimulation increased the number of neurons in all regions counted.

PCT Publication WO 01/85094 and US Patent Application Publications 2004/0015068 and 2004/0210269 to Shalev and Gross, which are assigned to the assignee of the present patent application and are incorporated herein by reference, describe apparatus for modifying a property of a brain of a patient, including electrodes applied to a sphenopalatine ganglion (SPG) or a neural tract originating in or leading to the SPG. A control unit drives the electrodes to apply a current capable of inducing (a) an increase in permeability of a blood-brain barrier (BBB) of the patient, (b) a change in cerebral blood flow of the patient, and/or (c) an inhibition of parasympathetic activity of the SPG.

PCT Publication WO 03/105658 to Shalev and US Patent Application Publication 2006/0020299 in the US national stage thereof, both of which are assigned to the assignee of the present application and are incorporated herein by reference, describe a method for treating Alzheimer's disease (AD). The method includes stimulating a sphenopalatine ganglion (SPG) of a subject so that the concentration of a substance in a brain of the subject changes. The publications also describe stimulating sphenopalatine ganglion (SPG)-related tissue of the subject by applying an electrical signal to the SPG-related tissue, and configuring the stimulation so as to cause an increase in cerebral blood flow (CBF) of the subject, so as to treat the AD.

U.S. Pat. No. 6,853,858 to Shalev, which is assigned to the assignee of the present application and is incorporated herein by reference, describes an apparatus for delivering a Non Steroidal Anti-Inflammatory Drug (NSAID) supplied to a body of a subject for delivery to at least a portion of a central nervous system (CNS) of the subject via a systemic blood circulation of the subject. The apparatus includes a stimulator adapted to stimulate at least one site of the subject, so as to cause an increase in passage of the NSAID from the systemic blood circulation across a blood brain barrier (BBB) of the subject to the portion of the CNS, during at least a portion of the time that the NSAID is present in the blood, the site selected from the group consisting of: a sphenopalatine ganglion (SPG), an anterior ethmoidal nerve, a posterior ethmoidal nerve, a communicating branch between an anterior ethmoidal nerve and a retro-orbital branch of an SPG, a communicating branch between a posterior ethmoidal nerve and a retro-orbital branch of an SPG, a greater palatine nerve, a lesser palatine nerve, a sphenopalatine nerve, a communicating branch between a maxillary nerve and an SPG, a nasopalatine nerve, a posterior nasal nerve, an infraorbital nerve, an otic ganglion, an afferent fiber going into the otic ganglion, an efferent fiber going out of the otic ganglion, a vidian nerve, a greater superficial petrosal nerve, and a lesser deep petrosal nerve.

US Patent Application Publication 2004/0220644 to Shalev et al., which is assigned to the assignee of the present application and is incorporated herein by reference, describes a method for treating a subject, including positioning at least one electrode at at least one site of the subject, such as the SPG, for less than about 3 hours, applying an electrical current to the site of the subject, and configuring the current to increase cerebral blood flow (CBF) of the subject, so as to treat a condition of the subject.

US Patent Application Publication 2003/0176898 to Gross et al., which is assigned to the assignee of the present application and is incorporated herein by reference, describes apparatus for treating a condition of an eye of a subject, comprising a stimulator adapted to stimulate at least one site of the subject, such as the SPG, so as to treat the eye condition.

US Patent Application Publication 2005/0159790 to Shalev, which is assigned to the assignee of the present application and is incorporated herein by reference, describes a method for facilitating a diagnosis of a condition of a subject, including applying a current to a site of the subject, such as the SPG, and configuring the current to increase conductance of molecules from brain tissue of the subject through a blood brain barrier (BBB) of the subject into a systemic blood circulation of the subject. The method also includes sensing a quantity of the molecules from a site outside of the brain of the subject, following initiation of application of the current.

US Patent Application Publication 2005/0266099 to Shalev, which is assigned to the assignee of the present application and is incorporated herein by reference, describes a method for modifying a property of a brain of a patient including presenting an odorant to an air passage of the patient, the odorant having been selected for presentation to the air passage because it is such as to increase conductance of molecules from a systemic blood circulation of the patient through a blood brain barrier (BBB) of the brain into brain tissue of the patient. The molecules are selected from the group consisting of: a pharmacological agent, a therapeutic agent, an endogenous agent, and an agent for facilitating a diagnostic procedure.

PCT Publication WO 04/010923 to Gross et al., which is assigned to the assignee of the present application and is incorporated herein by reference, describes a chemical agent delivery system, including a chemical agent supplied to a body of a subject for delivery to a site in a central nervous system of said subject via blood of said subject; and a stimulator for stimulating parasympathetic fibers associated with the SPG, thereby rendering a blood brain barrier (BBB) of said subject permeable to said chemical agent during at least a portion of the time that said chemical agent is present in said blood.

PCT Publication WO 04/043218 to Gross et al., which is assigned to the assignee of the present application and is incorporated herein by reference, describes apparatus for treating a subject, including (a) a stimulation device, adapted to be implanted in a vicinity of a site selected from the list consisting of: a SPG and a neural tract originating in or leading to the SPG; and (b) a connecting element, coupled to the stimulation device, and adapted to be passed through at least a portion of a greater palatine canal of the subject.

PCT Publication WO 04/045242 to Shalev, which is assigned to the assignee of the present application and is incorporated herein by reference, describes apparatus for treating a condition of an ear of a subject, comprising a stimulator adapted to stimulate at least one site of the subject, such as the SPG, at a level sufficient to treat the ear condition.

PCT Publication WO 05/030025 to Shalev et al., which is assigned to the assignee of the present application and is incorporated herein by reference, describes apparatus for treating a subject, including an elongated generally rigid support element having a length of at least 1.8 cm, and having a distal end. The apparatus also includes one or more electrodes fixed to the support element in a vicinity of the distal end thereof, and configured to be positioned in a vicinity of a site of the subject, such as the SPG, when the support element is inserted into a body of the subject, such that a portion of the support element remains outside of the body. The apparatus further includes a control unit, coupled to the support element, and adapted to drive the electrodes to apply an electrical current to the site, and to configure the current to increase cerebral blood flow (CBF) of the subject, so as to treat a condition of the subject.

U.S. Pat. No. 6,526,318 to Ansarinia and related PCT Publication WO 01/97905 to Ansarinia, which are incorporated herein by reference, describe a method for the suppression or prevention of various medical conditions, including pain, movement disorders, autonomic disorders, and neuropsychiatric disorders. The method includes positioning an electrode on or proximate to at least one of the patient's SPG, sphenopalatine nerves, or vidian nerves, and activating the electrode to apply an electrical signal to such nerve. In a further embodiment for treating the same conditions, the electrode used is activated to dispense a medication solution or analgesic to such nerve.

The following patent application publications, all of which are assigned to the assignee of the present application and are incorporated herein by reference, may be of interest: WO 03/090599, WO 04/010923, WO 04/043218, WO 04/044947, WO 04/045242, WO 04/043217, WO 04/043334, WO 05/030025, WO 05/030118, and US 2004/0220644.

The following patents and patent application publications, all of which are incorporated herein by reference, may be of interest: U.S. Pat. No. 5,756,071 to Mattern et al., U.S. Pat. No. 5,752,515 to Jolesz et al., U.S. Pat. Nos. 5,725,471 and 6,086,525 to Davey et al., PCT Publication WO 02/32504 to Zanger et al., US Patent Application Publication 2003/0050527 to Fox et al., U.S. Pat. No. 6,415,184 to Ishikawa et al., PCT Publications WO 03/084591, WO 03/020350, WO 03/000310, WO 02/068031, and WO 02/068029 to Djupesland, US Patent Application Publication 2003/0079742 to Giroux, U.S. Pat. No. 6,405,079 to Ansarinia, U.S. Pat. No. 6,432,986 to Levin and PCT Publication WO 99/03473 to Levin, U.S. Pat. No. 6,491,940 to Levin, US Patent Application 2003/0133877 to Levin, and PCT Publication WO 00/44432 to Levin, and US Patent Application 2001/0004644 to Levin and PCT Publication WO 01/43733 to Levin, Wilner A, in an article entitled, "Who is at risk for post-stroke dementia?" Neurology Reviews.com Vol. 11, No. 2 (February 2003), which is incorporated herein by reference, describes the results of a study analyzing risk factors for survival of a stroke and post-stroke dementia.

Hotta H et al., in an article entitled, "Effects of stimulating the nucleus basalis of Meynert on blood flow and delayed neuronal death following transient ischemia in rat cerebral cortes," Jap J Phys 52:383-393 (2002), which is incorporated herein by reference, report that stimulation of the nucleus basalis of Meynert (NBM) in the rat was accompanied by vasodilatation and increase in cortical blood flow. They suggest that NBM-originating vasodilative activation can protect the ischemia-induced delayed death of cortical neurons by preventing a blood flow decrease in widespread cortices.

Reis D J et al., in an article entitled, "Electrical stimulation of cerebellar fastigial nucleus reduces ischemic infarction elicited by middle cerebral artery occlusion in rat," J Cereb Blood Flow Metab 11(5):810-8 (1991), which is incorporated herein by reference, report that electrical stimulation of the cerebellar fastigial nucleus (FN) profoundly increases cerebral blood flow via a cholinergic mechanism. Utilizing the rat middle cerebral artery occlusion (MCAO) model, they demonstrated that one hour of electrical stimulation of the FN has the capacity to substantially reduce the infarct size at the rim of the cortex dorsal and ventral to the infarction, and medially within the thalamus and striatum corresponding to the penumbral zone. They conclude that excitation of an intrinsic system in brain represented in the rostral FN has the capacity to substantially reduce an ischemic infarction.

Matsui T et al., in an article entitled, "The effects of cervical spinal cord stimulation (cSCS) on experimental stroke," Pacing Clin Electrophysiol 12(4 Pt 2):726-32 (1989), which is incorporated herein by reference, report that cSCS increases regional cerebral blood flow, and, in a cat middle cerebral artery occlusion model (MCAO), reduced the rate of death within 24 hours after MCAO.

Segher O et al., in an article entitled, "Spinal cord stimulation reducing infract volume in model of focal cerebral ischemia in rats," J Neurosurg 99(1):131-137 (2003), which is incorporated herein by reference, demonstrate that spinal cord stimulation increases cerebral blood flow in rats and significantly reduces stroke volume, suggesting that spinal cord stimulation could be used for treatment and prevention of stroke.

The following references, which are incorporated herein by reference, may be useful:

Pullicino and Hart, "Cognitive impairment in congestive heart failure?: Embolism vs hypoperfusion," Neurology 57, 1945-1946 (2001)

Roman G C. The epidemiology of vascular dementia. In: Hatmen A, Kuchinsky W, Hoyer S, eds. Cerebral Ischemia and Dementia. Berlin: Springer-Verlag, 1991:9-15

Lobo A., Launer L J, Fratiglioni L, et al. Prevalence of dementia and major subtypes in Europe: a collaborative study of population-based cohorts. Neurologic Diseases in the Elderly Research Group. Neurology 2000; 54:S4-9

Ott A, Breteler M B, Harskamp F, et al. Prevalence of Alzheimer's disease and vascular dementia: association with education. The Rotterdam study. BMJ 1995; 310:970-973

White L, Petrovitch H, Ross G W, et al. Prevalence of dementia in older Japanese-American men in Hawaii: the Honolulu-Asia Aging Study. JAMA 1996; 276:955-960

Rocca W A, Bonaiuto S, Lippi A, et al. Prevalence of clinically diagnosed Alzheimer's disease and other dementing disorder: a door-to-door survey in Appignano, Marcerata Province, Italy. Neurology 1990; 46:626-631

Bachman D L, Wolf P A, Linn R T, et al. Incidence of dementia and probable Alzheimer's disease in a general population: The Framingham Study. Neurology 1993; 43:515-519

Sicras A, Rejas J, Arco S, et al. Prevalence, resource utilization and costs of vascular dementia in a population setting. Dement Geriatr Cogn Disord. 255; 19:305-315

Chui H. Vascular dementia, a new beginning: Shifting focus from clinical phenotype to ischemic brain injury. Neurol Clin 2000; 59:931-945

Roman G C, Tatemichi T K, Erkinjuntti T, et al. Vascular dementia: diagnostic criteria for research studies. Report of the NINDS-AIREN International Workshop. Neurology 1993; 43:250-260

Erkinjuntti T, Inzitari D, Pantoni L, et al. Research criteria for subcortical vascular dementia in clinical trials. Journal of neuronal Transmission Supp. 2000; 59:23-30

Pantoni L, Simoni M. Pathophysiology of cerebral small vessels in vascular cognitive impairment. Intl Psycogeriat 2003; 15(Supp 1):59-65

Brun A, Englund E. A white matter disorder in dementia of the Alzheimer type: A pathoanatomical study. Ann Neurol 1986; 19:253-262

Capizzano A A, Schuff N, Amend D L, et al. Subcortical ischemic vascular dementia: Assessment with quantitative MR imaging and H1 MR spectroscopy. AJNR 2000; 21:621-630

Hatchinski V C, Potter p, Merskey H. Leuko-araiosis. Arch Neurol 1987; 44:21-23

Meyer J S, Rogers R L, Judd B W, et al. Cognition and cerebral blood flow fluctuate together in multi-infarct dementia. Stroke 1988; 19:163-169

Mortel K F, Pavol M A, Wood S, et al. Prospective studies of cerebral perfusion and cognitive testing among elderly normal volunteers and patients with ischemic vascular dementia and Alzheimer's disease. Angiology 1994; 45:171-180

Yoshikawa T, Murase K, Oku N, et al. Quantification of the heterogeneity of cerebral blood flow in vascular dementia. J Neurol 2003; 250:194-200

Zimny A, Leszek J, Kiejna A, et al. Analysis of correlation between the degree of cognitive impairment and the results of perfusion CT in patients with dementia. Med Sci Monit 2007; 13(Supp 1): 23-30

Markus H S, Lythgoe D J, Ostegaard L, et al. Reduced cerebral blood flow in white matter in ischemic leukoaraiosis demonstrated using quantitative exogenous contrast based perfusion MRI. J Neurol Neurosurg Psychiatry 2000; 69:48-53

O'Sullivan M, Lythgoe D J, Pereira A C, et al. Patterns of cerebral blood flow reduction in patients with ischemic leukoaraiosis. Neurology 2002; 59:321-326

Meyer E, Delpla P, Pertides E, et al. PET metabolic and neuropsychological correlates of periventricular lucencies. In: Hatmen A, Kuchinsky W, Hoyer S, eds. Cerebral Ischemia and Dementia. Berlin: Springer-Verlag, 1991

Kawamura J, Meyer J S, Terayama Y, et al. Leukoaraiosis correlates with cerebral hypoperfusion in vascular dementia. Stroke 1991; 22:609-614

Schmidt R, Petrovic K, Ropele S, et al. Progression of leukoaraiosis and cognition. Stroke 2007; 38:2619-2625

Enzinger C, Fazekas F, Ropele S, et al. Progression of cerebral white matter lesions—Clinical and radiological considerations. J Neurol Sci 2007; 257:5-10

Schmidt R, Enzinger C, Ropele S, et al. Progression of cerebral white matter lesions: 6 years results of the Austrian Stroke Prevention Study. Lancet 2003; 361:2046-2048

Garde E, Mortensen E L, Rostrup E, et al. Decline in intelligence is associated with progression in white matter hyperintensity volume. J Neurol Neurosurg Psychiatry 2005; 76:1289-1291

Schmidt R, Ropele S, Enzinger C, et al. White matter lesion progression, brain atrophy, and cognitive decline: The Austrian Stroke Prevention Study. Ann Neurol 2005; 58:610-616

Bombois S, Debette S, Delbeuck X, et al. Prevalence of subcortical vascular lesions and association with executive function in mild cognitive impairment subtypes. Stroke 2007; 38:2595-2597

Price C C, Jefferson A L, Merino J G, et al. Subcortical vascular dementia: Integrating neuropsychological and neuroradiologic data. Neurology 2005; 65:376-382

Lojkowska W, Ryglewicz D, Jedrzejczak T, et al. The effect of cholinesterase inhibitors on the regional blood flow in patients with Alzheimer's disease and vascular dementia. J Neurol Sci 2003; 216:119-126

Delepine L, Aubineau P, "Plasma protein extravasation induced in the rat dura mater by stimulation of the parasympathetic sphenopalatine ganglion," Experimental Neurology, 147, 389-400 (1997)

Hara H, Zhang Q J, Kuroyanagi T, Kobayashi S, "Parasympathetic cerebrovascular innervation: An anterograde tracing from the sphenopalatine ganglion in the rat," Neurosurgery, 32, 822-827 (1993)

Jolliet-Riant P, Tillement J P, "Drug transfer across the blood-brain barrier and improvement of brain delivery," Fundam. Clin. Pharmacol., 13, 16-25 (1999)

Kroll R A, Neuwelt E A, "Outwitting the blood brain barrier for therapeutic purposes: Osmotic opening and other means," Neurosurgery, 42, 1083-1100 (1998)

Syelaz J, Hara H, Pinard E, Mraovitch S, MacKenzie E T, Edvinsson L, "Effects of stimulation of the sphenopalatine ganglion on cortical blood flow in the rat," Journal of Cerebral Blood Flow and Metabolism," 8, 875-878 (1988)

Van de Waterbeemd H, Camenisch G, Folkers G, Chretien J R, Raevsky O A, "Estimation of blood brain barrier crossing of drugs using molecular size and shape and h bonding descriptors," Journal of Drug Targeting," 6, 151-165, (1998)

Suzuki N, Hardebo J E, Kahrstrom J, Owman C, "Selective electrical stimulation of postganglionic cerebrovascular parasympathetic nerve fibers originating from the sphenopalatine ganglion enhances cortical blood flow in the rat," Journal of Cerebral Blood Flow and Metabolism, 10, 383-391 (1990)

Suzuki N, Hardebo J E, Kahrstrom J, Owman C H, "Effect on cortical blood flow of electrical stimulation of trigeminal cerebrovascular nerve fibres in the rat," Acta Physiol. Scand., 138, 307-315 (1990)

Major A, Silver W, "Odorants presented to the rat nasal cavity increase cortical blood flow," Chem. Senses, 24, 665-669 (1999)

Fusco B M, Fiore G, Gallo F, Martelletti P, Giacovazzo M, "'Capsaicin-sensitive' sensory neurons in cluster headache: pathophysiological aspects and therapeutic indications," Headache, 34, 132-137 (1994)

Lambert G A, Bogduk N, Goadsby P J, Duckworth J W, Lance J W, "Decreased carotid arterial resistance in cats in response to trigeminal stimulation," Journal of Neurosurgery, 61, 307-315 (1984)

Silver W L, "Neural and pharmacological basis for nasal irritation," in Tucker W G, Leaderer B P, Mølhave L, Cain W S (eds), Sources of Indoor Air Contaminants, Ann. NY Acad. Sci., 641, 152-163 (1992)

Silver W, "Chemesthesis: the burning questions," ChemoSense, Vol. 2, 1-2 (1999)

Devoghel J C, "Cluster headache and sphenopalatine block," Acta Anaesthesiol Belg., 32(1):101-7 (1981)

Branston N M, "The physiology of the cerebrovascular parasympathetic innervation," British Journal of Neurosurgery 9:319-329 (1995)

Branston N M et al., "Contribution of cerebrovascular parasympathetic and sensory innervation to the short-term control of blood flow in rat cerebral cortex," J Cereb Blood Flow Metab 15(3):525-31 (1995)

Toda N et al., "Cerebral vasodilation induced by stimulation of the pterygopalatine ganglion and greater petrosal nerve in anesthetized monkeys," Neuroscience 96(2):393-398 (2000)

Seylaz J et al., "Effect of stimulation of the sphenopalatine ganglion on cortical blood flow in the rat," J Cereb Blood Flow Metab 8(6):875-8 (1988)

Nollet H et al., "Transcranial magnetic stimulation: review of the technique, basic principles and applications," The Veterinary Journal 166:28-42 (2003)

Van Gijn J et al., "Subarachnoid haemorrhage: diagnosis, causes and management," Brain 124:249-278 (2001)

Goadsby P J et al., "Effect of stimulation of trigeminal ganglion on regional cerebral blood flow in cats," Am J Physiol 22:R270-R274 (1987)

Walters B B et al., "Cerebrovascular projections from the sphenopalatine and otic ganglia to the middle cerebral artery of the cat," Stroke 17:488-494 (1986)

Suzuki N et al., "Trigeminal fibre collaterals storing substance P and calcitonin gene-related peptide associate with ganglion cells containing choline acetyltransferase and vasoactive intestinal polypeptide in the sphenopalatine ganglion of the rat. An axon reflex modulating parasympathetic ganglionic activity?" Neuroscience 30:595-604 (1989)

Roth B J et al., "In vitro evaluation of a 4-leaf coil design for magnetic stimulation of peripheral nerve," Electroencephalography and Clinical Neurophysiology 93:68-74 (1994)

Zhang R et al., "A nitric oxide donor induces neurogenesis and reduces functional deficits after stroke in rats," Ann Neurol 50:602-611 (2001)

Ziche M et al., "Nitric oxide and angiogenesis," J Neurooncol 50:139-148 (2000)

Kawamata T et al., "Intracisternal basic fibroblast growth factor (bFGF) enhances behavioral recovery following focal cerebral infarction in the rat," J Cereb Blood Flow Metab 16:542-547 (1996)

Zhang Z G et el., "VEGF enhances angiogenesis and promotes blood-brain barrier leakage in the ischemic brain," J Clin Invest 106:829-838 (2000)

Sun Y et al., "Neuronal nitric oxide synthase and ischemia-induced neurogenesis," J Cereb Blood Flow Metab 25(4): 485-92 (2005)

Zhang F et al., "Nitric oxide donors increase blood flow and reduce brain damage in focal ischemia: evidence that nitric oxide is beneficial in the early stages of cerebral ischemia," J Cereb Blood Flow Metab 14(2):217-26 (1994)

Beridze M et al., "Effect of nitric oxide initial blood levels on erythrocyte aggregability during 12 hours from ischemic stroke onset," Clin Hemorheol Microcirc 30(3-4):403-6 (2004)

Davis S M et al., "Advances in penumbra imaging with MR," Cerebrovasc Dis 17 Suppl 3:23-7 (2004)

Phan T G et al., "Salvaging the ischaemic penumbra: more than just reperfusion?" Clin Exp Pharmacol Physiol 29(1-2):1-10 (2002)

Gressens P et al., "Neuroprotection of the developing brain by systemic administration of vasoactive intestinal peptide derivatives," J Pharmacol Exp Ther 288 (3):1207-13 (1999)

Zhang R et al., "Nitric oxide enhances angiogenesis via the synthesis of vascular endothelial growth factor and cGMP after stroke in the rat," Circ Res 21; 92(3):308-13 (2003)

de la Torre J C, "Vascular basis of Alzheimer's pathogenesis," Ann NY Acad Sci 977:196-215 (2002)

Roman G C, "Cholinergic dysfunction in vascular dementia," Curr Psychiatry Rep 7(1):18-26 (2005)

Tony J F L, "Nitric oxide and the cerebral vascular function," J Biomed Sci 7:16-26 (2000)

Pluta R M, "Delayed cerebral vasospasm and nitric oxide: review, new hypothesis, and proposed treatment," Pharmacol Ther 105(1):23-56 (2005)

Sandgren K et al., "Vasoactive intestinal peptide and nitric oxide promote survival of adult rat myenteric neurons in culture," J Neurosci Res 72(5):595-602 (2003)

Laude K et al., "NO produced by endothelial NO synthase is a mediator of delayed preconditioning-induced endothelial protection," Am J Physiol Heart Circ Physiol 284(6): H2053-60 (2003) (Epub Jan. 9, 2003)

Khan M et al., "S-Nitrosoglutathione reduces inflammation and protects brain against focal cerebral ischemia in a rat model of experimental stroke," J Cereb Blood Flow Metab 25(2):177-92 (2005)

Molloy J et al., "S-nitrosoglutathione reduces the rate of embolization in humans," Circulation 98(14):1372-5 (1998)

Schmid-Elsaesser R et al., "A critical reevaluation of the intraluminal thread model of focal cerebral ischemia. Evidence of inadvertent premature reperfusion and subarachnoid hemorrhage in rats by laser-Doppler flowmetry," Stroke 29:2162-2170 (1998)

Zausinger V S et al., "Neurological impairment in rats after transient middle cerebral artery occlusion: a comparative study under various treatment paradigms," Brain Research 863(1-2):94-105 (2000)

Hunter A J et al., "To what extent have functional studies of ischemia in animals been useful in the assessment of potential neuroprotective agents?" Trends Pharmacol Sci 19:59-66 (1998)

Varghese et al., "Endoscopic transnasal neurolytic sphenopalatine ganglion block for head and neck cancer pain," J Laryngol Otol 115(5):385-7 (2001)

Kanner A A et al., "Serum S100beta: a noninvasive marker of blood-brain barrier function and brain lesions," Cancer 97(11):2806-13 (2003)

SUMMARY OF THE INVENTION

In some embodiments of the present invention, an electrical stimulation system is provided for reducing the risk of vascular dementia (VaD). The system is configured to apply excitatory electrical stimulation to at least one "modulation target site" (MTS), as defined hereinbelow, such as a sphenopalatine ganglion (SPG). The system applies the stimulation chronically, and configures the stimulation to augment cerebral blood perfusion to hypoperfused brain regions, and/or to release of one or more neuroprotective substances. Such stimulation generally reduces the risk of development of VaD, i.e., delays or prevents the impending VaD.

In some embodiments of the present invention, a method for using the system comprises identifying that a subject is at risk of suffering from VaD, and reducing the risk by applying stimulation to at least one MTS using the system. For some applications, the method comprises identifying that the subject already suffers from minimal cognitive impairment or vascular cognitive impairment. Alternatively, the subject may suffer from low cerebral blood perfusion, even without any clinical signs of minimal cognitive impairment, vascular cognitive impairment, or other VaD. Furthermore, for some applications, the method comprises identifying that an elderly subject displaying no symptoms of VaD is at risk, and applying the MTS stimulation in order to postpone the subject's normally expected decline in cerebral blood flow (CBF). For some applications, the method comprises identifying that the subject suffers from one or more symptoms of a vascular disorder, such as hypertension, peripheral vascular disease, or coronary artery disease. Alternatively or additionally, the method comprises identifying that the subject suffers from reduced cardiac output, e.g., caused by heart failure.

In some embodiments of the present invention, the VaD includes post-stroke dementia, which develops in about one-third of stroke victims within three months after suffering from a stroke. In addition to identifying that the subject has suffered from the stroke, identifying that the subject is at risk of post-stroke dementia may comprise assessing an age of the subject at the time of stroke, a severity of the stroke, whether the subject suffers from hypertension, whether the stroke has recurred, and/or an indication of cognitive function of the subject during the acute state of the stroke.

The stimulation is typically applied on a chronic, long-term basis, i.e., for at least one week, such as at least two weeks, at least four weeks, at least three months, at least six months, or during the remaining life of the subject. During this chronic treatment, stimulation is typically applied intermittently, such as during one session per day, or less frequently, such as depending on the severity of assessed risk. Alternatively, the stimulation is applied generally constantly, typically at a low strength. For some applications, the stimulation is applied bilaterally to both SPGs, while for other applications, the stimulation is applied unilaterally, such as to the MTS (e.g., the SPG) that supplies the more affected hemisphere of the brain.

In some embodiments of the present invention, these techniques are used for preventing the dementia associated with Alzheimer's disease.

In some embodiments of the present invention, a method is provided for preventing CBF deterioration in a subject who has not been diagnosed with any neurological condition associated with reduced CBF. The method comprises identifying that the subject may be at risk of suffering from reduced CBF, and applying chronic, long-term stimulation to an MTS, such as the SPG. The subject may be at risk of suffering the reduced CBF in the future, or may be at risk of already suffering from undiagnosed reduced CBF. The chronic stimulation has a duration of at least two weeks, at least four weeks, at least three months, at least six months, or the remaining life of the subject. During this chronic treatment, stimulation is typically applied intermittently, such as during one session per day, or less frequently, such as depending on the severity of assessed risk. Alternatively, the stimulation is applied generally constantly, typically at a low strength.

For some applications, identifying that the subject is at risk of suffering the reduced CBF comprises identifying that the subject is at least a threshold age. For example, the threshold age may be between about 50 and about 80 years. Alternatively or additionally, the subject may identified as at risk of reduced CBF because the subject suffers from one or more symptoms of a vascular disorder, such as hypertension, peripheral vascular disease, or coronary artery disease. Alternatively or additionally, the method comprises identifying that the subject suffers from reduced cardiac output, e.g., caused by heart failure. Further alternatively or additionally, the subject is determined to be at risk of suffering from reduced CBF if the subject has a family history of any type of dementia, and/or the subject has radiological findings suggestive of cerebral vascular disease or Alzheimer's disease.

In some embodiments of the present invention, the method comprises assessing a level of CBF of a subject who has not been diagnosed with any neurological condition associated with reduced CBF, and applying chronic stimulation responsively to finding that the assessed level is less than a threshold level. Some techniques for measuring CBF are described hereinbelow. For some applications, assessing comprises quantitatively assessing the level of CBF, while for other applications, assessing comprises non-quantitatively assessing the level of CBF, such as by observing a physiological characteristic of the subject.

In some embodiments of the present invention, stimulation of an MTS, such as the SPG, is applied to treat a subject already suffering from VaD. The stimulation generally treats the VaD by stopping or slowing the progression of the dementia, and for some subjects improves cognitive ability.

In the present patent application, a "modulation target site" (MTS) consists of:
an SPG (also called a pterygopalatine ganglion);
a nerve of the pterygoid canal (also called a vidian nerve), such as a greater superficial petrosal nerve (a preganglionic parasympathetic nerve) or a lesser deep petrosal nerve (a postganglionic sympathetic nerve);
a greater palatine nerve;
a lesser palatine nerve;
a sphenopalatine nerve;
a communicating branch between the maxillary nerve and the sphenopalatine ganglion;
an otic ganglion;
an afferent fiber going into the otic ganglion;
an efferent fiber going out of the otic ganglion; or
an infraorbital nerve.

It is to be appreciated that references herein to specific modulation target sites are to be understood as including other modulation target sites, as appropriate.

It is further to be appreciated that insertion and modulation sites, methods of insertion and/or implantation, and parameters of modulation are described herein by way of illustration and not limitation, and that the scope of the present invention includes other possibilities which would be obvious to someone of ordinary skill in the art who has read the present patent application.

It is yet further to be appreciated that while some embodiments of the invention are generally described herein with respect to electrical transmission of power and electrical modulation of tissue, other modes of energy transport may be used as well. Such energy includes, but is not limited to, direct or induced electromagnetic energy, radiofrequency (RF) transmission, mechanical vibration, ultrasonic transmission, optical power, and low power laser energy (via, for example, a fiber optic cable).

It is additionally to be appreciated that whereas some embodiments of the present invention are described with respect to application of electrical currents to tissue, this is to be understood in the context of the present patent application and in the claims as being substantially equivalent to applying an electrical field, e.g., by creating a voltage drop between two electrodes.

In embodiments of the present invention, treating an adverse brain event or condition typically includes identifying that a subject is suffering from, and/or has suffered from, the brain event or condition.

There is therefore provided, in accordance with an embodiment of the present invention, a method including:
identifying that a subject is at risk of suffering from vascular dementia (VaD); and
responsively to the identifying, reducing a risk of development of the VaD by:
applying electrical stimulation to a site of the subject selected from the group consisting of: a sphenopalatine ganglion (SPG), a greater palatine nerve, a lesser palatine nerve, a sphenopalatine nerve, a communicating branch between a maxillary nerve and an SPG, an otic ganglion, an afferent fiber going into the otic ganglion, an efferent fiber going out of the otic ganglion, an infraorbital nerve, a vidian nerve, a greater superficial petrosal nerve, and a lesser deep petrosal nerve, and
configuring the stimulation to induce at least one neuroprotective occurrence selected from the group consisting of: an increase in cerebral blood flow (CBF) of the subject, and a release of one or more neuroprotective substances.

Typically, applying the stimulation comprises applying the stimulation at least intermittently (i.e., intermittently or generally constantly) during a period having a duration of at least four weeks.

For some applications, identifying includes identifying that the subject suffers from cognitive impairment selected from the group consisting of: minimal cognitive impairment, and vascular cognitive impairment. For some applications, identifying includes identifying that the subject suffers from low cerebral blood perfusion. For some applications, identifying includes identifying that the subject is at risk even though the subject displays no symptoms of VaD. Alternatively or additionally, identifying includes identifying that the subject suffers from reduced cardiac output.

For some applications, configuring the stimulation includes setting a strength of the stimulation to be less than 40% of a strength that induces a maximum increase in CBF in the subject that is achievable by applying the stimulation. Alternatively or additionally, configuring the stimulation includes setting a strength of the stimulation to a level that induces less than 40% of a maximum increase in CBF in the subject that is achievable by applying the stimulation.

For some applications, applying the stimulation includes placing, e.g., implanting, an electrical stimulator in a vicinity of the site, and activating the stimulator to apply the stimulation.

In an embodiment, the site includes the SPG, and applying the stimulation includes applying the stimulation to the SPG.

In an embodiment, the VaD includes post-stroke dementia, and identifying includes identifying that the subject has suffered from a stroke.

For some applications, identifying includes assessing an age of the subject at a time of the stroke, assessing a severity of the stroke, identifying that the subject suffers from hypertension, identifying that the stroke has recurred, and/or assessing an indication of cognitive function of the subject during an acute stage of the stroke.

In an embodiment, applying the stimulation includes applying the stimulation during a plurality of stimulation periods which includes at least first and last stimulation periods, and setting an inter-period interval between initiation of the first stimulation period and initiation of the last stimulation period to be at least one week. For some applications, the initiation of the last stimulation period occurs simultaneously with a conclusion of the first stimulation period, and applying the stimulation during the first and last stimulation periods includes applying the stimulation continuously from the initiation of the first stimulation period to a conclusion of the last stimulation period. For some applications, the initiation of the last stimulation period occurs after a conclusion of the first stimulation period, and applying the stimulation during the first and last stimulation periods includes withholding applying the stimulation during at least one non-stimulation period between the conclusion of the first stimulation period and the initiation of the last stimulation period.

In an embodiment, configuring the stimulation includes setting a strength of the stimulation to be insufficient to induce a significant increase in permeability of a blood-brain barrier (BBB) of the subject. For some applications, setting the strength includes setting the strength of the stimulation to be less than 40% of a strength that is sufficient to induce the significant increase in permeability of the BBB.

For some applications, the at least one neuroprotective occurrence includes the increase in the CBF, and configuring includes configuring the stimulation to induce the increase in the CBF.

Typically, applying the electrical stimulation includes applying excitatory electrical stimulation to the site.

There is further provided, in accordance with an embodiment of the present invention, a method including:

identifying that a subject may be at risk of suffering from reduced cerebral blood flow (CBF), which subject, at a time of the identifying, has not been diagnosed with any neurological condition associated with the reduced CBF; and responsively to the identifying, applying excitatory electrical stimulation to a site of the subject at least intermittently during a period having a duration of at least four weeks, the site selected from the group consisting of: a sphenopalatine ganglion (SPG), a greater palatine nerve, a lesser palatine nerve, a sphenopalatine nerve, a communicating branch between a maxillary nerve and an SPG, an otic ganglion, an afferent fiber going into the otic ganglion, an efferent fiber going out of the otic ganglion, an infraorbital nerve, a vidian nerve, a greater superficial petrosal nerve, and a lesser deep petrosal nerve, and configuring the stimulation to induce an increase in the CBF of the subject.

For some applications, identifying that the subject may be at risk includes identifying that the subject is at least a threshold age. For example, the threshold age may be between 50 and 80 years.

For some applications, identifying that the subject may be at risk includes identifying the existence of at least one state selected from the group consisting of: the subject suffering from a non-cerebral vascular disorder, the subject suffering from hypertension, the subject suffering from peripheral vascular disease, the subject suffering from coronary artery disease, the subject having a family history of any type of dementia, and the subject suffering from reduced cardiac output.

In an embodiment, the site includes the SPG, and applying the stimulation includes applying the stimulation to the SPG.

Alternatively, a subject may be identified as at risk of suffering from reduced CBF is the subject has radiological findings suggestive of cerebral vascular disease or Alzheimer's disease.

There is still further provided, in accordance with an embodiment of the present invention, a method including:

assessing a level of cerebral blood flow (CBF) of a subject who does not suffer from any clinical signs related to reduced CBF at a time of the assessing;

comparing the assessed level to a threshold level; and upon finding that the assessed level is less than the threshold level, applying excitatory electrical stimulation to a site of the subject at least intermittently during a period having a duration of at least four weeks, the site selected from the group consisting of: a sphenopalatine ganglion (SPG), a greater palatine nerve, a lesser palatine nerve, a sphenopalatine nerve, a communicating branch between a maxillary nerve and an SPG, an otic ganglion, an afferent fiber going into the otic ganglion, an efferent fiber going out of the otic ganglion, an infraorbital nerve, a vidian nerve, a greater superficial petrosal nerve, and a lesser deep petrosal nerve, and configuring the stimulation to induce an increase in the CBF of the subject.

In an embodiment, the site includes the SPG, and applying the stimulation includes applying the stimulation to the SPG.

There is additionally provided, in accordance with an embodiment of the present invention, a method comprising:

identifying that a subject is at risk of suffering from Alzheimer's disease; and responsively to the identifying, reducing a risk of development of the Alzheimer's disease by:

applying electrical stimulation to a site of the subject selected from the group consisting of: a sphenopalatine ganglion (SPG), a greater palatine nerve, a lesser palatine nerve, a sphenopalatine nerve, a communicating branch between a maxillary nerve and an SPG, an otic ganglion, an afferent fiber going into the otic ganglion, an efferent fiber going out of the otic ganglion, an infraorbital nerve, a vidian nerve, a greater superficial petrosal nerve, and a lesser deep petrosal nerve, and configuring the stimulation to induce at least one neuroprotective occurrence selected from the group consisting of: an increase in cerebral blood flow (CBF) of the subject, and a release of one or more neuroprotective substances.

In an embodiment, the site includes the SPG, and applying the stimulation comprises applying the stimulation to the SPG.

The present invention will be more fully understood from the following detailed description of the embodiments thereof, taken together with the drawings, in which:

DETAILED DESCRIPTION OF EMBODIMENTS

Figure 1:
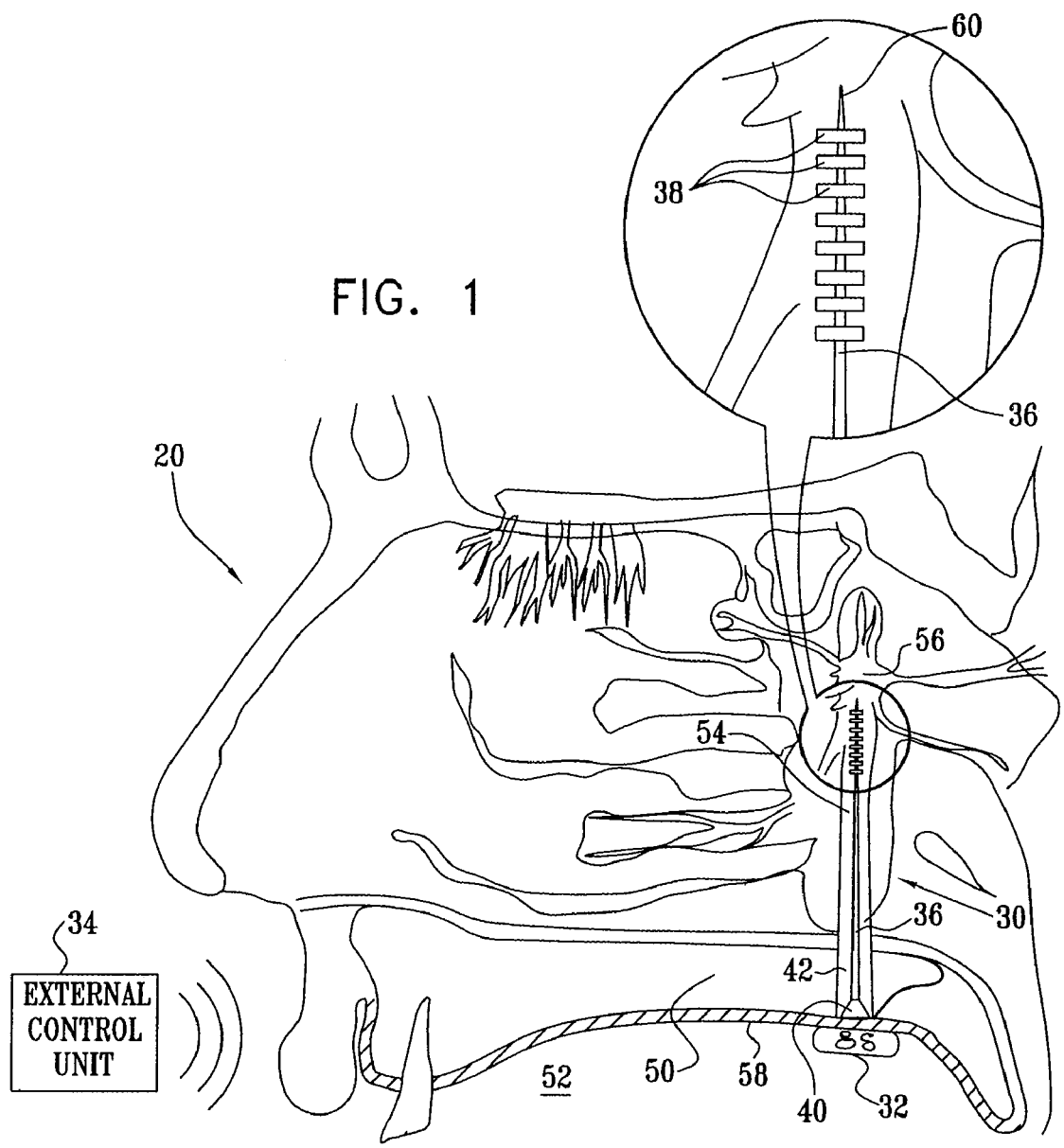
FIG. 1 is a schematic illustration of a neural stimulation system, in accordance with an embodiment of the present invention.

FIG. 1 is a schematic illustration of a neural stimulation system 20, in accordance with an embodiment of the present invention. System 20 typically comprises an implantable neural stimulator 30, an oral element 32, and an external control unit 34. Stimulator 30 comprises an elongated support element 36, one or more electrodes 38 fixed to the support element in a vicinity of a distal end thereof, and circuitry 40 coupled to the support element in a vicinity of a proximal end thereof. Circuitry 40 typically comprises a wireless coupling element (which typically comprises a coil), and additional elements, such as one or more rectifiers, capacitors, amplifiers, or filters. One or more leads (not shown in FIG. 1), which pass along, through, or around support element 36, couple electrodes 38 to circuitry 40. Alternatively, the leads function as the support element, i.e., the support element does not comprise any structural elements in addition to the leads. Further alternatively, the leads provide a substantial portion of the structural support of the support element, and the balance of the structural support is provided by other elements. For example, support element 36 may comprise the leads and a flexible sleeve surrounding the leads; the leads supply most of the structural support of the support element, while the sleeve allows smooth passage of the leads through the greater palatine canal. Circuitry 40 is shown schematically in FIG. 1; the circuitry may employ one or more of the more detailed configurations described with reference to FIGS. 3A-B, 4A-B, and 5A-D of U.S. patent application Ser. No. 11/349,020, filed Feb. 7, 2006, entitled, "SPG stimulation via the greater palatine canal," which is assigned to the assignee of the present application and is incorporated herein by reference.

Stimulator 30 is adapted to be passed through a greater palatine foramen 42 of a hard palate 50 of an oral cavity 52 of a subject into a greater palatine canal 54, such that electrodes 38 are brought into a vicinity of a sphenopalatine ganglion (SPG) 56. For some applications, the entire stimulator is contained within greater palatine canal 54, while for other applications, at least a portion of the circuitry and/or the support element are positioned submucosally in the oral cavity. For clarity of illustration, the greater and lesser palatine nerves, and the greater and less palatine arteries are not shown in the figures. During an implantation procedure, stimulator 30 is typically passed through greater palatine foramen 42 posterior to the greater palatine nerve and artery, which are manipulated into an anterior position within the canal.

For some applications, electrodes 38 apply a monophasic waveform to SPG 56, while for other applications, electrodes 38 apply a biphasic waveform. Alternatively or additionally, waveforms and/or stimulation techniques may be used that are described in one or more of the patent applications incorporated by reference hereinbelow, or waveforms and/or stimulation techniques may be used that are known in the art of neural stimulation.

Figure 2:
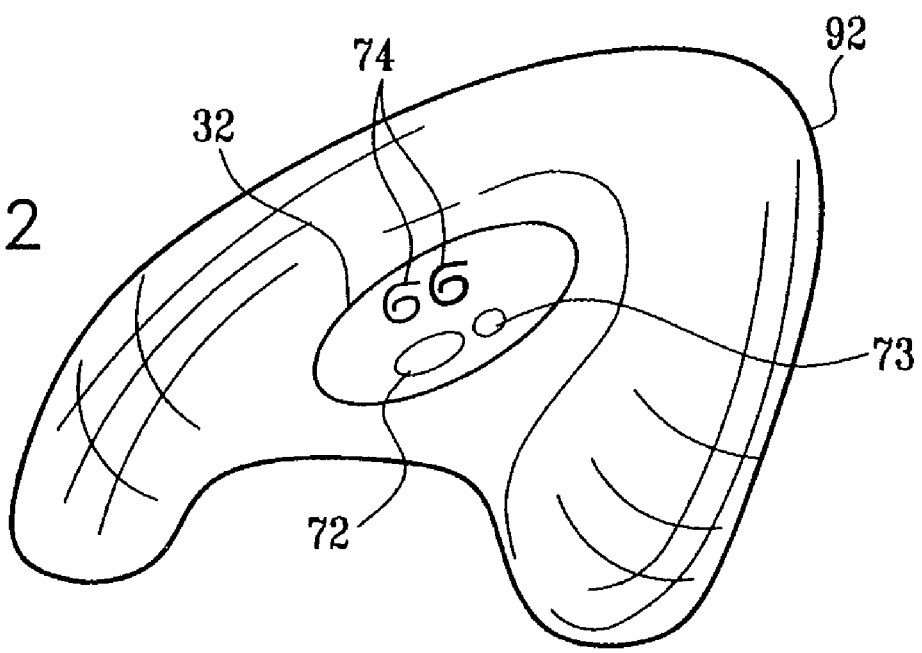
FIG. 2 is a schematic illustration of an oral element of the system of FIG. 1 coupled to an oral appliance, in accordance with an embodiment of the present invention.

FIG. 2 is a schematic illustration of oral element 32 coupled to an oral appliance 92, in accordance with an embodiment of the present invention. Oral appliance 92, which is typically shaped generally similarly to an orthodontic retainer, is configured to hold the oral element in a vicinity of or in contact with the roof of the oral cavity in a vicinity of implanted circuitry 40 of stimulator 30. The use of oral appliance 92, rather than mechanical coupling of oral element 32 to the roof of the oral cavity, generally reduces the likelihood of contamination. For some applications, oral appliance 92 is generally soft or semi-flexible, while for other applications, the oral appliance is generally rigid.

For some applications, oral element 32 does not comprise power source 72. Instead, power is provided by a power source located outside of the oral cavity. For example, the oral appliance may be coupled by a cable to an external driver comprising a power source. For some applications, the driver is coupled to a headset or necklace worn by the subject. The driver or a separate external control unit, instead of oral element 32, comprises all or a portion of circuitry 73. For some applications, the driver is coupled to external control unit 34, while for other applications, the driver comprises external control unit 34. Alternatively, oral element 32 is wirelessly coupled to external control unit 34, which may or may not be coupled to the external driver.

In an embodiment of the present invention, system 20 comprises a nasal element instead of or in addition to oral element 32 (configuration not shown). The nasal element is adapted to be inserted into a nostril of the subject, e.g., into the nasal vestibule. The nasal element comprises at least one wireless coupling element 74 that is wirelessly coupled to transmit/receiver 40 of stimulator 30, for transmitting/receiving power and/or data to/from the stimulator. In this embodiment, circuitry 40 of stimulator 30 is not necessarily positioned at the proximal end of the stimulator.

For some applications, circuitry 40 of stimulator 30 comprises a wireless coupling element. Wireless coupling element 74 of oral element 32 is adapted to wirelessly transmit energy and/or data to the wireless coupling element of circuitry 40, and/or to wirelessly receive data form the wireless coupling element of circuitry 40. For these applications, each of the wireless coupling elements typically comprises at least one coil. For some applications, the wireless coupling elements are wirelessly coupled to one another using induction, such as when the wireless coupling elements are positioned in close proximity to one another. Alternatively, the wireless coupling elements are wirelessly coupled to one another using RF energy, such as when the wireless coupling elements are positioned at a greater distance from each other. Further alternatively, the wireless coupling elements are wirelessly coupled to one another using another form of energy, such as ultrasound energy, in which case the wireless coupling elements comprises ultrasound transducers, e.g., piezoelectric transducers. "Transducer element," as used in the present application including the claims, means an element adapted to wirelessly transmit and/or receive energy and/or data, including a coil, a piezoelectric transducer, and other wireless transducers known in the art.

In an embodiment of the present invention, oral element 32 does not comprise wireless coupling element 74. Instead, power source 72 of the oral element is coupled to circuitry 40 using a wire that passes through mucosa 58. The techniques of this embodiment are generally more energy-efficient than wireless energy/data transfer techniques. As a result, the battery of power source 72 of oral element 32 may need to be replaced or recharged less frequently, or not at all. For some applications, oral element 32 is adapted to be implanted in a tooth of the subject. For some applications, the implanted oral element comprises a wireless communication element for external wireless communication, such as of data. For some applications, power source 72 comprises a rechargeable or a replaceable battery.

Figure 3:
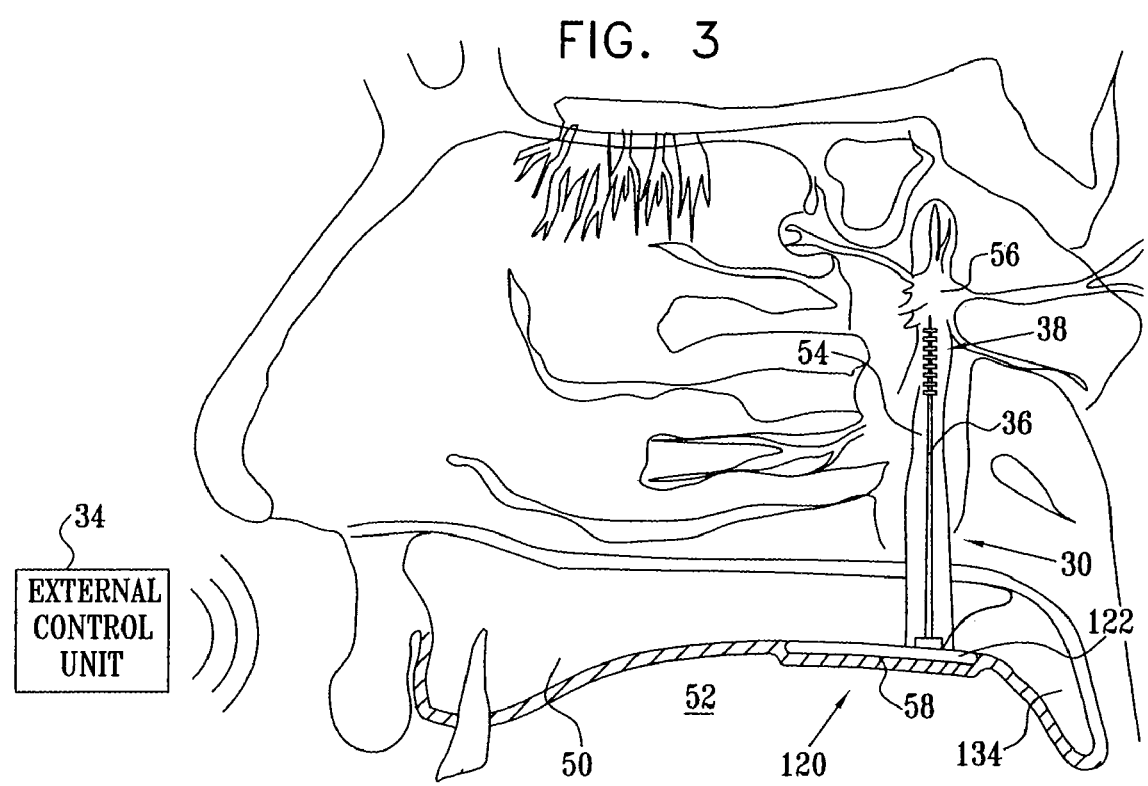
FIG. 3 is a schematic illustration of another neural stimulation system, in accordance with an embodiment of the present invention.

Reference is made to FIG. 3, which is a schematic illustration of a neural stimulation system 120, in accordance with an embodiment of the present invention. Except as noted hereinbelow, elements of system 120 are the same as corresponding elements of system 20 having the same reference numerals. System 120 comprises implantable neural stimulator 30 and external control unit 34. Stimulator 30 comprises elongated support element 36, one or more electrodes 38 fixed to the support element in the vicinity of the distal end thereof, and an implantable submucosal antenna 122 coupled to the support element in a vicinity of the proximal end thereof. Submucosal antenna 122 is configured to be implanted in the roof of oral cavity 52 between oral mucosa 58 and a palate, e.g., hard palate 50 and/or a soft palate 134, and to generally conform to the shape of the palate.

For some applications, the level of stimulation of the SPG is determined by assessing an indirect physiological parameter of the subject related to the level of SPG stimulation, such as cerebral blood flow (CBF) and/or BBB permeability. For some applications, assessment techniques described hereinbelow are used. For some applications, a healthcare worker enters the values of the indirect physiological parameter into system 20, while for other applications, a device for measuring the indirect physiological parameters is coupled to system 20, and communicates the parameters to the system.

Although electrodes 38 have been described as being applied to an SPG of the subject, for some applications the electrodes are applied to another MTS of the subject, as defined hereinabove. For some of these applications, electrodes 38 are passed through the greater palatine canal to the MTS, while for other applications the electrodes are passed through only a portion of the greater palatine canal, or are advanced to the MTS by another route.

In an embodiment of the present invention, system 20 is used to reduce the risk of vascular dementia (VaD). System 20 is configured to apply excitatory electrical stimulation to at least one MTS, as defined hereinabove, such as SPG 56. The system applies the stimulation chronically, and configures the stimulation to augment cerebral blood perfusion to hypoperfused brain regions, by dilating cerebral vessels, thereby increasing cerebral blood flow (CBF) to brain tissue. Alternatively or additionally, the stimulation causes the release of one or more neuroprotective substances, such as neuromodulators (e.g., nitric oxide (NO) and/or vasoactive intestinal polypeptide (VIP)). Such stimulation generally reduces the risk of development of VaD, i.e., delays or prevents the impending VaD. Typically, the VaD includes vascular cognitive impairment (VCI), multi-infarct dementia, strategic single-infarct dementia, post-stroke dementia, small vessel disease (SVD) (leukoaraiosis), or a combination of more than one type of VaD (mixed VaD).

In an embodiment of the present invention, a method for using system 20 comprises identifying that a subject is at risk of suffering from VaD, and applying the stimulation responsively to the identifying. For some applications, the method comprises identifying that the subject already suffers from vascular cognitive impairment or minimal cognitive impairment. For some applications, identifying that the subject is at risk of suffering from VaD comprises analyzing a radiological imaging status of the subject. Recent large scale prospective studies (for a review see Schmidt R et al. (2007), cited in the Background of the Invention) indicated that leukoaraiosis progresses over time and that its extent at baseline is an important predictor for the subsequent rate of lesion progression (Enzinger C et al., Schmidt R et al. (2003)). For instance, individuals with early confluent and confluent leukoaraiotic changes tend to progress rapidly. Moreover, the progression of leukoaraiosis closely relates to the rate of cognitive decline (Garde E et al., Schmidt R et al. (2005)), and especially the decline in executive functions.

For some applications, system 20 is used to apply stimulation to a subject that suffers from low cerebral blood perfusion, even without any clinical signs of minimal cognitive impairment, minimal cognitive impairment, or other VaD. Such subjects are often at greater risk for developing VaD (see, for example, Meyer J S et al.). For example, low cerebral blood perfusion may be detected using the indicators of CBF described hereinbelow, using SPECT or CT/MRI perfusion techniques known in the art, and/or using other techniques known in the art.

For some applications, the method comprises identifying that an elderly subject displaying no symptoms of VaD is at risk, and applying the stimulation in order to postpone the subject's normally expected decline in cerebral blood flow (CBF). For some applications, the method comprises identifying that the subject suffers from reduced cardiac output, e.g., caused by heart failure (see, for example, Pullicino et al. (2001)).

In an embodiment of the present invention, the VaD includes post-stroke dementia, which develops in about one-third of stroke victims within three months after suffering from a stroke. In addition to identifying that the subject has suffered from the stroke, identifying that the subject is at risk of post-stroke dementia may comprise assessing an age of the subject at the time of stroke, a severity of the stroke, whether the subject suffers from hypertension, whether the stroke has recurred, and/or an indication of cognitive function of the subject during the acute state of the stroke.

The stimulation is typically applied on a chronic, long-term basis, i.e., for at least one week, such as at least two weeks, at least four weeks, at least three months, at least six months, or longer, such as for the remainder of the subject's life. During this chronic treatment, stimulation is typically applied intermittently, such as during one session per day, or less frequently, such depending on the severity of assessed risk. For some applications, each session has a duration of between 1 minute and 6 hours, such as at least 5 minutes or at least 15 minutes, or between 2 and 4 hours, e.g., about 3 hours or about 6 hours, or more than 6 hours. Alternatively, the system is configured to apply such stimulation generally constantly, i.e., 24 hours per day. Further alternatively, the stimulation is applied less frequently than every day, such as once every other day (e.g., at least one minute during every 48 hours), or more frequently than once per day, such as during two sessions per day.

For some applications, the stimulation is applied during a plurality of stimulation periods which includes at least first and last stimulation periods. System 20 sets an inter-period interval between initiation of the first period and initiation of the last period to be at least 24 hours. For example, the first stimulation period may occur from 1:00 P.M. to 4:00 P.M. on a Monday, and the last stimulation period may occur from 1:00 P.M. to 4:00 P.M. on a Tuesday of the same week. Optionally, stimulation is applied during at least one additional stimulation period between the first and last periods. For example, stimulation may be additionally applied from 1:00 A.M. to 4:00 A.M. on the Tuesday. For some applications, the first period concludes simultaneously with the initiation of the last period, i.e., the stimulation is applied constantly from the beginning of the first period until the conclusion of the last period. For example, the stimulation may be applied constantly from 1:00 P.M. on Monday, January 1 to 4:00 P.M. on Tuesday, January 2, or constantly from 1:00 P.M. on Monday, January 1 to 4:00 P.M. on Monday, January 29. Alternatively, the initiation of the last stimulation period occurs after a conclusion of the first stimulation period, such that the stimulation is not applied during at least one non-stimulation period between the conclusion of the first stimulation period and the initiation of the last stimulation period.

For some applications, the system sets the inter-period interval to be at least 48 hours, such as at least one week, at least two weeks, or at least four weeks. When using such greater inter-period intervals, the system typically, but not necessarily, applies stimulation during at least several additional stimulation periods between the first and last stimulation periods. For some applications, such additional stimulation periods may include a plurality of daily stimulation periods, applied on every day between the initiation of the first stimulation period and the initiation of the last stimulation period. For example, the first stimulation period may occur from 1:00 P.M. to 4:00 P.M. on Monday, January 1, the last stimulation period may occur from 1:00 P.M. to 4:00 P.M. on Monday, January 8, and the additional daily stimulation periods may occur from 1:00 P.M. to 4:00 P.M. on each day from Tuesday, January 2 through Sunday, January 7, inclusive. For some applications, stimulation is applied for at least 30 minutes every day (e.g., at least 60 minutes every day) between the initiation of the first stimulation period and the initiation of the last stimulation period. For some applications, stimulation is applied during a plurality of non-continuous stimulation periods during each 24-hour period between the initiation of the first stimulation period and the initiation of the last stimulation period. For example, the first stimulation period may occur from 1:00 P.M. to 4:00 P.M. on Monday, the last stimulation period may occur from 1:00 P.M. to 4:00 P.M. on Wednesday, and stimulation may be applied during additional stimulation periods from (a) 1:00 A.M. to 4:00 A.M. on Tuesday, (b) from 1:00 P.M. to 4:00 P.M. on Tuesday, and (c) from 1:00 A.M. to 4:00 A.M. on Wednesday, such that stimulation is applied during two stimulation periods during the 24-hour period from 1:00 P.M. on Monday to 1:00 P.M. on Tuesday, and during two stimulation periods during the 24-hour period from 1:00 P.M. on Tuesday to 1:00 P.M. on Wednesday.

For some applications, the system is configured to set the inter-period interval to be no more than a maximum value, such as three, six, nine, or twelve months. For some applications, the system comprises a user interface, which enables a healthcare worker to enter a value for the inter-period interval. The system typically rejects values that are greater than the maximum value, such as by requiring the healthcare worker to enter another value, or by using the maximum value instead of the entered value. Alternatively, the system notifies the healthcare worker if the entered value is greater than the maximum value; optionally, the system allows the healthcare worker to override the notification.

For some applications, the system is configured to store a maximum total time of stimulation per each time period having a given duration, and to apply the stimulation no more than the maximum total time per each time period having the given duration. For example, the given duration of each time period may be 24 hours. Typical values for the maximum total time of stimulation per 24-hour period include one hour, three hours, six hours, ten hours, and twelve hours. For some applications, the maximum total time of stimulation is predetermined, e.g., by the manufacturer of the system, while for other applications, a healthcare worker enters the maximum total time of stimulation into the system.

As used in the present application, including the claims, a "stimulation period" includes an entire period during which stimulation is applied, even though current is applied to the site only during a portion of the period, because of the duty cycle, on/off periods, and/or frequency of the current, for example.

For some applications, the stimulation is applied bilaterally to both SPGs, while for other applications, the stimulation is applied unilaterally to the MTS (e.g., the SPG) that supplies the more affected hemisphere of the brain. For some applications in which the stimulation is applied bilaterally, techniques are used that are described in U.S. application Ser. No. 11/573,993, filed Feb. 19, 2007, entitled, "Concurrent bilateral SPG modulation," which is assigned to the assignee of the present application and is incorporated herein by reference.

In some embodiments of the present invention, stimulation of an MTS, such as the SPG, is applied to treat a subject already suffering from VaD. The stimulation generally stops or slows the progression of the dementia, and for some subjects improves cognitive ability.

Figure 4:
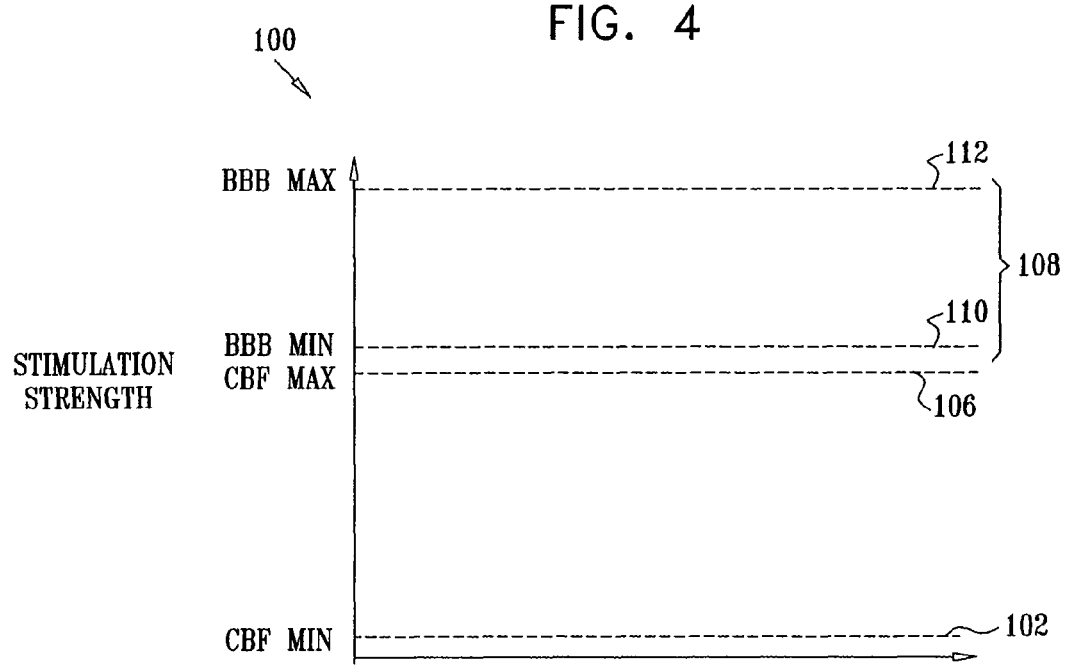
FIG. 4 is a graph illustrating electrical stimulation strengths, in accordance with an embodiment of the present invention.

Reference is made to FIG. 4, which is a graph 100 illustrating electrical stimulation strengths, in accordance with an embodiment of the present invention. Excitatory stimulation of an MTS (e.g., the SPG) induces changes in CBF, induces the release of one or more neuroprotective substances, such as neuromodulators (e.g., nitric oxide (NO) and/or vasoactive intestinal polypeptide (VIP)), and/or modulates permeability of the blood-brain barrier (BBB). The inventors have found that excitatory stimulation of an MTS at at least a minimum threshold strength increases CBF, and that the increase in CBF is related to the strength of the stimulation. The inventors have also found that at a sufficiently high strength, such stimulation modulates the permeability of the BBB, in addition to increasing CBF.

"Strength," as used in the present application, including the claims, means a total charge applied to an MTS in a given time period, e.g., one minute, one hour, or one day. Strength is increased or decreased by changing one or more parameters of the applied stimulation, such as the amplitude, number of cycles in a given time period, frequency, pulse width, or duty cycle (e.g., ratio of "on" to "off" time within a given cycle), as described hereinbelow in greater detail.

The y-axis of graph 100 indicates the strength of the stimulation of an MTS. The strength of the stimulation is determined by the values of the parameters of the stimulation, such as voltage, current, frequency, cycles per time period, and duty cycle. Stimulation at at least a minimum CBF-increasing strength 102 increases CBF. Stimulation at such a strength also typically induces the release of one or more neuroprotective substances, such as NO and/or VIP. A maximum CBF-increasing strength 106 is the strength at which CBF is maximally increased, i.e., further increases in strength do not further increase CBF. The BBB is opened, i.e., the permeability of the BBB to larger molecules or substances that do not cross the intact BBB is significantly increased, by stimulation having a strength in a range 108 between a minimum BBB-opening strength 110 and maximum BBB-opening strength 112 (beyond which increased strength does not result in additional opening of the BBB). Although minimum BBB-opening strength 110 is shown in graph 100 as being greater than maximum CBF-increasing strength 106, this is not necessarily the case.

In the present application, including the claims, stimulation of an MTS is considered capable of inducing a "significant" increase in the permeability of the BBB if the stimulation is capable of inducing at least one of the following:

(a) an increase in concentration of Evans blue (EB) in brain tissue of a subject, such as a rat, of at least 100% compared to a baseline concentration measured in a control rat. To determine the increase, permanent middle cerebral artery occlusion (pMCAO) is induced in the rat, such as using techniques described hereinbelow with reference to FIG. 6. Three hours after pMCAO, stimulation is applied to the MTS, and a bolus of EB 2% at 1 ml per kg body weight of the rat is administered intravenously. The rat is sacrificed one hour after application of the stimulation and administration of the EB. To determine the baseline concentration, pMCAO is induced in a control rat, three hours after pMCAO an identical EB bolus is administered intravenously, but no stimulation is applied, and the control rat is sacrificed one hour after the administration of the EB; and (b) a serum S100beta level of the subject (indicative of clearance of the protein from the brain into the systemic circulation), at a measurement time 45 minutes after initiation of MTS stimulation, that is at least 30% greater than a serum S100beta level of the subject measured at the beginning of the MTS stimulation.

Although the above are indications of the "significance" of an increase in permeability of the BBB, use of the apparatus and performance of the methods described and claimed herein typically do not include measuring any of these indications. In particular, indication (a) is generally only possible to measure in an animal model; if it were desired to conduct a human experiment, different techniques would likely be used, such as measuring the concentration in the brain of a radioactive isotope that is normally excluded by the BBB.

For some applications, it is desirable to apply stimulation to an MTS, and configure the stimulation to have a strength that induces an increase in permeability of the BBB that is even lower than a "significant" increase, as defined above. Such a "sub-significant" increase in permeability of the BBB is considered to occur if the stimulation is capable of inducing at least one of the following: (i) an increase in concentration of EB, under the conditions defined in indication (a) above, of at least 20%, such as at least 30%, e.g., at least 50%; and (ii) a serum S100beta level, under the conditions defined in indication (b) above, that is at least 10%, e.g., at least 20%, greater than the level of the subject measured at the beginning of the MTS stimulation.

For some applications, it is useful to define increased CBF as a percentage increase in CBF over a baseline level of CBF, which increase has at least a certain duration, e.g., at least 5 minutes. Typically, the baseline CBF level is either: (a) a normal baseline level for a subject, i.e., prior to an adverse brain event, such as a cerebrovascular event, e.g., a stroke, or (b) a post-event baseline level, prior to stimulation using the techniques described herein, and, optionally, prior to other treatment of the event. CBF is typically expressed as volume of blood flow per time per mass of the subject, e.g., ml/min/ 100 g. For some applications, increased CBF is expressed as an area under the curve (AUC) of CBF with respect to baseline over a certain time interval.

In an embodiment of the present invention, electrical stimulation system 20 is configured to apply excitatory electrical stimulation to at least one MTS of a subject, and to configure the stimulation to increase CBF of the subject and/ or induce the release of neuroprotective substances, without substantially opening the BBB of the subject. In other words, the system sets the strength of stimulation equal to less than minimum BBB-opening strength 110, such as less than 90% of minimum BBB-opening strength 110, e.g., less than 80%, 70%, or 60% of minimum BBB-opening strength 110. For some applications, the system is configured to increase CBF of the subject and/or induce the release of neuroprotective substances without increasing the permeability of the BBB to a level that produces a measurably-harmful clinical effect for the subject.

The following table shows exemplary parameter ranges for some of the stimulation strengths and treatment protocols described hereinabove.

TABLE 1

| Indication | Signal amplitude | Hz | Pulse width (μsec) | No. of Cycles per hour | Cycle on/off time (sec) |
|---|---|---|---|---|---|
| Prevention of VaD | 0.5-10 mA | 10-30 | 100-500 | 1-10 | 60/12, 4/15, 30/60 |
| Minimum BBB | 1-4 V | 10-30 | 100-500 | 1-100 | 45/45, 45/90, 90/60, |
| Maximum BBB | 3.5-8 V | 10-50 | | | 4/15, 2/8 |

As indicated in Table 1, for some applications system 20 provides stimulation by applying a plurality of cycles of stimulation, each cycle including an "on" period (e.g., between 2 and 90 seconds) followed by an "off" period (e.g., between 8 and 90 seconds). Such cycles are applied a certain number of times per hour, typically spaced evenly throughout the hour. For example, if the cycles are applied four times per hour, the four cycles may be applied at the beginning of the hour, 15 minutes into the hour, 30 minutes into the hour, and 45 minutes into the hour, respectively. For some applications, each stimulation is applied in sets of two or more cycles. For example, if the stimulation is applied four times per hour, a set of two cycles may be applied at the beginning of the hour, 15 minutes into the hour, 30 minutes into the hour, and 45 minutes into the hour, respectively.

In an embodiment of the present invention, during placement of electrodes 38 at an MTS, as defined hereinabove, at least one physiological indicator of cerebral blood flow (CBF) is observed or measured concurrently with or after placement. For some applications, optimization of placement of electrodes 38 onto the appropriate neural structure is performed by activating the stimulator, and generally simultaneously monitoring CBF while manipulating the electrodes, and/or adjusting at least one parameter of the applied stimulation, so as to increase or decrease CBF, as appropriate. Alternatively or additionally, this technique is used to verify the placement of electrodes 38 after implantation, and/or to select which combination of electrodes to use, such as by using the feedback algorithm described hereinabove. Alternatively or additionally, a similar optimization process is performed, either during or after placement of electrodes 38, to determine parameters of the applied current so as to achieve a desired effect, e.g., on CBF or BBB permeability, as indicated by CBF.

Physiological indicators of CBF include, but are not limited to, the following:
- a measure of vasodilation of blood vessels of the eye, determined by unaided visual inspection or by using an instrument, e.g., an instrument comprising machine vision functionality;
- transcranial Doppler ultrasonography measurements;
- a measure of forehead perfusion, measured, for example, using laser Doppler perfusion imaging (LDI) and/or using a temperature sensor; and/or
- near infrared spectroscopy (NIRS) measurements.
- carotid artery duplex ultrasound Other appropriate measurements indicative of CBF for use with these embodiments of the present invention will be apparent to those skilled in the art, having read the disclosure of the present patent application.

For some applications, one or more of the devices described hereinbelow with reference to FIGS. 5-8 are used for assessing a physiological indicator of CBF.

Figure 5:
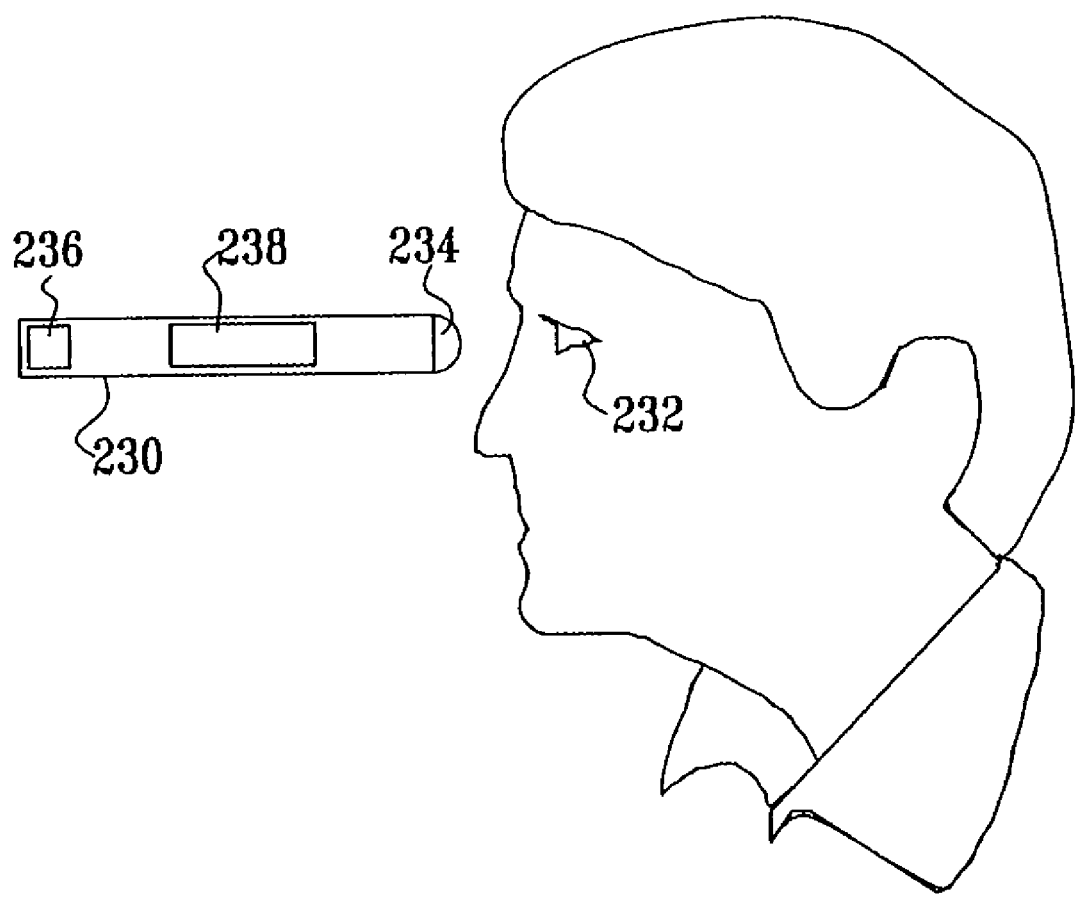
FIG. 5 is a schematic illustration of a vasodilation measurement instrument, in accordance with an embodiment of the present invention.

FIG. 5 is a schematic illustration of a vasodilation measurement instrument 230, in accordance with an embodiment of the present invention. Instrument 230 comprises an image sensor 234 (e.g., a CCD or CMOS sensor, or another camera) and processing circuitry 238, in order to provide machine vision functionality. Image sensor 234 is directed towards an eye 232 of the subject. The instrument measures the ratio of red to white in the sclera of eye 232, or another indication of vasodilation.

Figure 6:
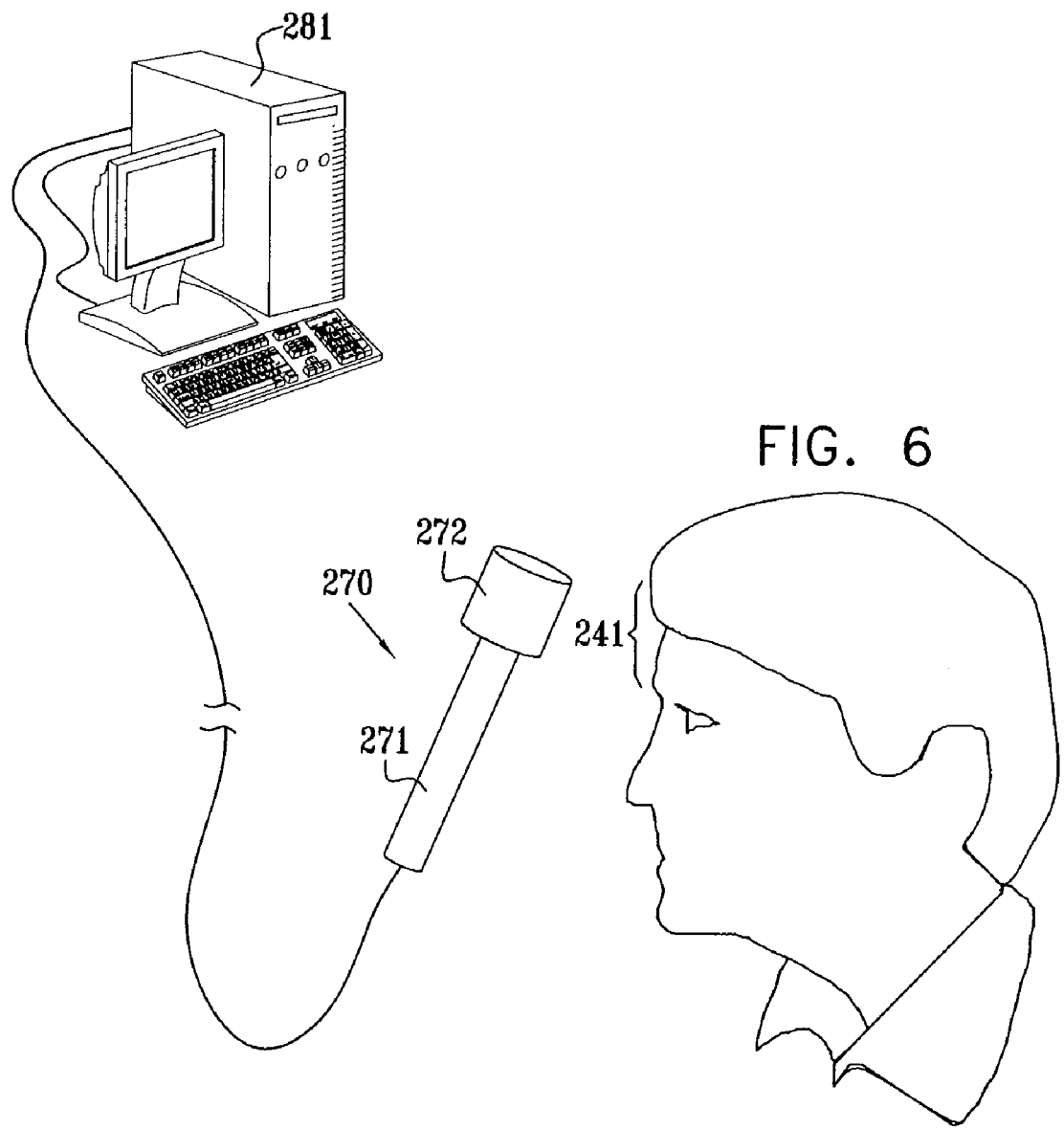
FIG. 6 is a schematic illustration of a laser Doppler imaging (LDI) device, in accordance with an embodiment of the present invention.

FIG. 6 is a schematic illustration of a laser Doppler perfusion (LDI) device 270, in accordance with an embodiment of the present invention. LDI device 270 comprises a laser source 271, a scanner 272, and a computer 281. Scanner 272 is positioned near a forehead 241 of the subject for measuring forehead perfusion.

Figure 7:
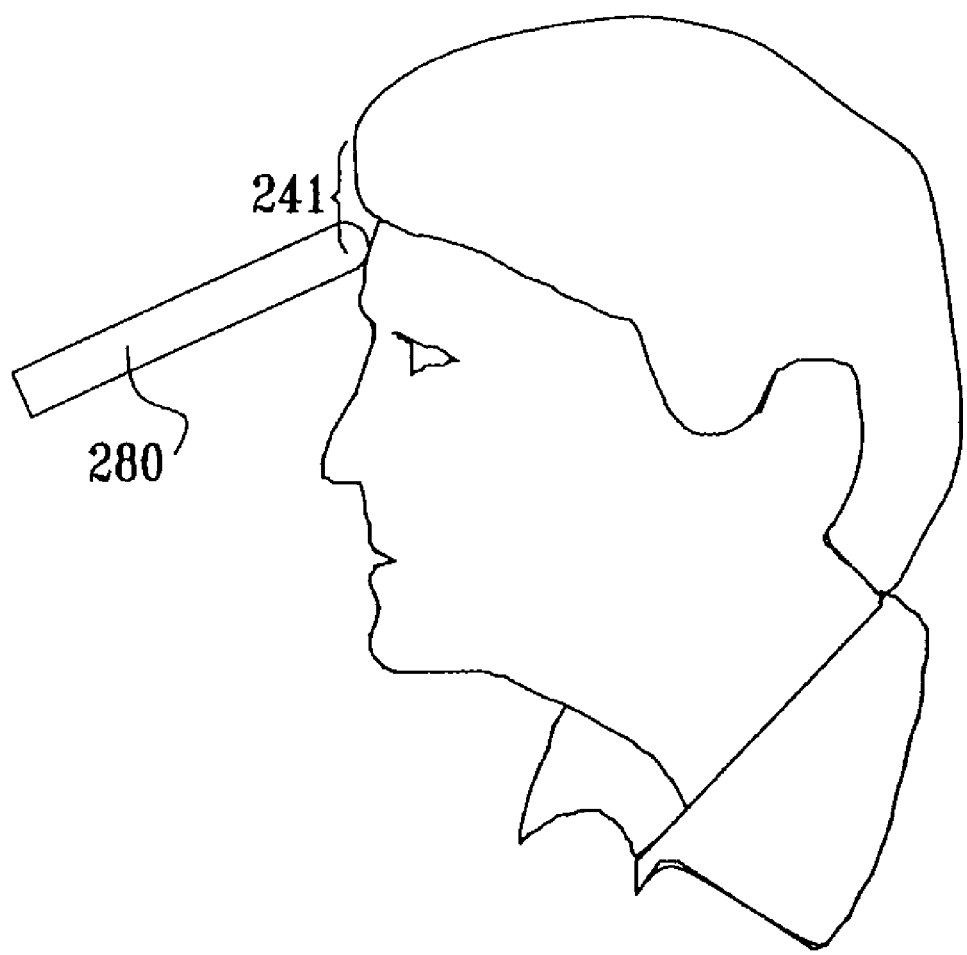
FIG. 7 is a schematic illustration of a thermometer, in accordance with an embodiment of the present invention.

FIG. 7 is a schematic illustration of a thermometer 280, in accordance with an embodiment of the present invention. Thermometer 280 is positioned touching a forehead 241 of the subject for measuring forehead perfusion.

Figure 8:
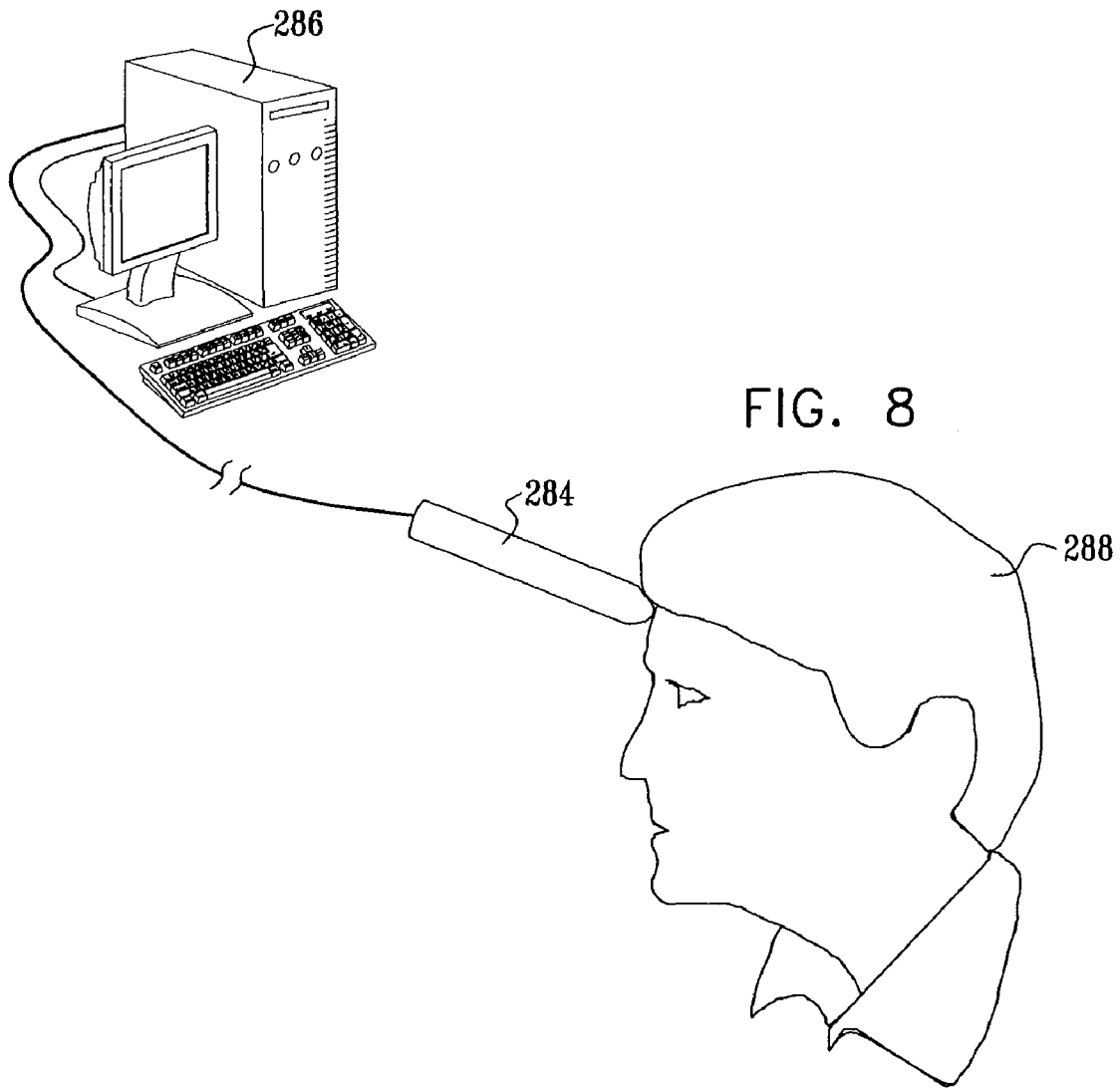
FIG. 8 is a schematic illustration of a transcranial Doppler ultrasonography device, in accordance with an embodiment of the present invention.

FIG. 8 is a schematic illustration of a transcranial Doppler ultrasonography device 284, in accordance with an embodiment of the present invention. Transcranial Doppler ultrasonography device 284 is positioned touching a head 288 of the subject for measuring CBF.

For some applications, the measurement device, such as those described hereinabove with reference to FIGS. 5-8, comprises an output unit 236, such as a numeric display, tone generator, color display, or other output device, for outputting a signal indicative of the measured physiological parameter. Alternatively or additionally, instrument 230 is coupled to an internal or external control unit of system 20 or 120, and communicates the signal directly to the control unit.

In an embodiment of the present invention, during placement of electrodes 38 at an MTS, as defined hereinabove, penetration of a systemically administered dye into an eye of the subject is observed or measured concurrently with or after placement, as an indication of a level of increased permeability of the BBB. For example, the dye may include fluorescein dye. For some applications, optimization of placement of electrodes 38 onto the appropriate neural structure is performed by activating the stimulator, and generally simultaneously monitoring the penetration of the dye while manipulating the electrodes, and/or adjusting at least one parameter of the applied stimulation, so as to increase or decrease permeability of the BBB, as appropriate. Alternatively or additionally, this technique is used to verify the placement of electrodes 38 after implantation, and/or to select which combination of electrodes to use, such as by using the feedback algorithm described hereinabove. Alternatively or additionally, a similar optimization process is performed, either during or after placement of electrodes 38, to determine parameters of the applied current so as to achieve a desired effect, e.g., on CBF or BBB permeability, as indicated by BBB permeability.

In an embodiment of the present invention, one or more of the above-described CBF-based assessment techniques are used by a healthcare worker after implantation to assess (a) whether electrodes 38 retain appropriate placement and contact with the MTS, and/or (b) whether parameters of the applied current (e.g., magnitude, frequency, duration, scheduling) continue to achieve the desired effect, e.g., on CBF or BBB permeability. For example, such an assessment may be performed periodically during post-implantation follow-up care.

In an embodiment of the present invention, the CBF-based assessment techniques described hereinabove are used to assist in determining the effective dosage and/or other parameters for presenting odorants to an air passage of the patient, as described in U.S. patent application Ser. No. 10/512,780, filed Oct. 25, 2004, which is assigned to the assignee of the present application and is incorporated herein by reference.

It is also to be appreciated that whereas some embodiments of the present invention are described with respect to implanting the electrical stimulator, for some applications the stimulator is temporarily or permanently inserted into the subject, and techniques described herein are used to optimize the temporary placement of the stimulator.

As appropriate, placement of stimulator 30 may be facilitated by fluoroscopy, x-ray guidance, fine endoscopic surgery (FES) techniques or by any other effective guidance method known in the art, or by combinations of the aforementioned. Typically, skin temperature and/or cerebral blood flow (CBF) is measured concurrently with insertion. CBF may be measured with, for example, a laser Doppler unit positioned at the patient's forehead or transcranial Doppler measurements. Verification of proper implantation of the electrodes onto the appropriate neural structure may be performed by activating the device, and generally simultaneously monitoring CBF. For some applications, stimulator 30 is implanted using techniques described in U.S. patent application Ser. No. 10/535,024, filed Dec. 27, 2005, entitled, "Surgical tools and techniques for stimulation," which is assigned to the assignee of the present application and is incorporated herein by reference, and/or in the above-mentioned PCT Publication WO 04/043218. For some applications, techniques described herein are performed in combination with apparatus and/or methods that are described in above-mentioned U.S. patent application Ser. No. 11/349,020.

In an embodiment of the present invention, techniques described herein are performed in conjunction with techniques described in US Patent Application Publication 2004/0220644, which is assigned to the assignee of the present application and is incorporated herein by reference.

In an embodiment of the present invention, a calibration procedure is performed, in which a test molecule is injected into the systemic blood circulation of the subject, and a threshold stimulation strength is determined by stimulating at least one MTS, and gradually increasing the stimulation strength until the BBB is opened (e.g., as determined using a radioactive scanning technique). System 20 applies therapeutic stimulation to an MTS using a strength equal to a certain percentage of the threshold strength, typically less than 100%.

In an embodiment of the present invention, bipolar stimulation is applied, in which a first electrode is applied to a first MTS, and a second electrode is applied to a second MTS.

In some embodiments of the present invention, techniques described herein are practiced in combination with techniques described in one or more of the references cited in the Background of the Invention section hereinabove and/or in combination with techniques described in one or more of the patent applications cited hereinabove.

In some embodiments of the present invention, chemical stimulation of at least one MTS is achieved by presenting chemicals, for example in a liquid or gaseous state, to an air passage of the subject, such as a nasal cavity or a throat, or in a vicinity thereof. The temporal profile and other quantitative characteristics of such chemical modulation are believed by the present inventors to have a mechanism of action that has a neuroanatomical basis overlapping with that of the electrical modulation of the MTS. For some applications, chemical-presentation techniques described herein are practiced in combination with techniques described in PCT Patent Application PCT/IL03/00338, filed Apr. 25, 2003 and/or a US patent application filed Sep. 27, 2005, entitled, "Stimulation for treating and diagnosing conditions," both of which are assigned to the assignee of the present patent application and are incorporated herein by reference.

The scope of the present invention includes embodiments described in the following patent applications, which are assigned to the assignee of the present patent application and are incorporated herein by reference. In an embodiment of the present invention, techniques and apparatus described in one or more of the following applications are combined with techniques and apparatus described herein:

U.S. Provisional Patent Application 60/203,172, filed May 8, 2000, entitled, "Method and apparatus for stimulating the sphenopalatine ganglion to modify properties of the BBB and cerebral blood flow"

U.S. patent application Ser. No. 10/258,714, filed Oct. 25, 2002, entitled, "Method and apparatus for stimulating the sphenopalatine ganglion to modify properties of the BBB and cerebral blood flow," or the above-referenced PCT Publication WO 01/85094

U.S. Provisional Patent Application 60/364,451, filed Mar. 15, 2002, entitled, "Applications of stimulating the sphenopalatine ganglion (SPG)"

U.S. Provisional Patent Application 60/368,657, filed Mar. 28, 2002, entitled, "SPG Stimulation"

U.S. Provisional Patent Application 60/376,048, filed Apr. 25, 2002, entitled, "Methods and apparatus for modifying properties of the BBB and cerebral circulation by using the neuroexcitatory and/or neuroinhibitory effects of odorants on nerves in the head"

U.S. Provisional Patent Application 60/388,931, filed Jun. 14, 2002, entitled "Methods and systems for management of Alzheimer's disease," PCT Patent Application PCT/IL03/000508, filed Jun. 13, 2003, claiming priority therefrom, and a US patent application filed Dec. 14, 2004 in the national stage thereof U.S. Provisional Patent Application 60/400,167, filed Jul. 31, 2002, entitled, "Delivering compounds to the brain by modifying properties of the BBB and cerebral circulation"

U.S. Provisional Patent Application 60/426,180, filed Nov. 14, 2002, entitled, "Surgical tools and techniques for sphenopalatine ganglion stimulation," PCT Patent Application PCT/IL03/000966, filed Nov. 13, 2003, which claims priority therefrom, and a US patent application filed May 11, 2005 in the national stage thereof U.S. Provisional Patent Application 60/426,182, filed Nov. 14, 2002, and corresponding PCT Patent Application PCT/IL03/000967, which claims priority therefrom, filed Nov. 13, 2003, entitled, "Stimulation circuitry and control of electronic medical device," and a US patent application filed May 11, 2005 in the national stage thereof U.S. patent application Ser. No. 10/294,310, filed Nov. 14, 2002, entitled, "SPG stimulation for treating eye pathologies," which published as US Patent Application Publication 2003/0176898, and PCT Patent Application PCT/IL03/000965, filed Nov. 13, 2003, claiming priority therefrom PCT Patent Application PCT/IL03/000631, filed Jul. 31, 2003, entitled, "Delivering compounds to the brain by modifying properties of the BBB and cerebral circulation," which published as PCT Publication WO 04/010923, and U.S. patent application Ser. No. 10/522,615 in the national stage thereof U.S. Pat. No. 6,853,858 to Shalev U.S. patent application Ser. No. 10/783,113, filed Feb. 20, 2004, entitled, "Stimulation for acute conditions," which published as US Patent Application Publication 2004/0220644

U.S. Provisional Patent Application 60/426,181, filed Nov. 14, 2002, entitled, "Stimulation for treating ear pathologies," PCT Patent Application PCT/IL03/000963, filed Nov. 13, 2003, which claims priority therefrom, and which published as PCT Publication WO 04/045242, and U.S. patent application Ser. No. 10/535,025 in the national stage thereof U.S. Provisional Patent Application 60/448,807, filed Feb. 20, 2003, entitled, "Stimulation for treating autoimmune-related disorders of the CNS"

U.S. Provisional Patent Application 60/461,232 to Gross et al., filed Apr. 8, 2003, entitled, "Treating abnormal conditions of the mind and body by modifying properties of the blood-brain barrier and cephalic blood flow"

PCT Patent Application PCT/IL03/00338 to Shalev, filed Apr. 25, 2003, entitled, "Methods and apparatus for modifying properties of the BBB and cerebral circulation by using the neuroexcitatory and/or neuroinhibitory effects of odorants on nerves in the head," and U.S. patent application Ser. No. 10/512,780, filed Oct. 25, 2004 in the national stage thereof, which published as US Patent Application 2005/0266099

U.S. Provisional Patent Application 60/506,165, filed Sep. 26, 2003, entitled, "Diagnostic applications of stimulation"

U.S. patent application Ser. No. 10/678,730, filed Oct. 2, 2003, entitled, "Targeted release of nitric oxide in the brain circulation for opening the BBB," which published as US Patent Application 2005/0074506, and PCT Patent Application PCT/IL04/000911, filed Oct. 3, 2004, claiming priority therefrom PCT Patent Application PCT/IL04/000897, filed Sep. 26, 2004, entitled, "Stimulation for treating and diagnosing conditions," which published as PCT Publication WO 05/030025

U.S. Provisional Patent Application 60/604,037, filed Aug. 23, 2004, entitled, "Concurrent bilateral SPG modulation"

PCT Patent Application PCT/IL05/000912, filed Aug. 23, 2005, entitled, "Concurrent bilateral SPG modulation," which published as PCT Publication WO 06/021957

U.S. patent application Ser. No. 10/952,536, filed Sep. 27, 2004, entitled, "Stimulation for treating and diagnosing conditions," which published as US Patent Application Publication 2005/0159790

U.S. patent application Ser. No. 11/349,020, filed Feb. 7, 2006, entitled, "SPG stimulation via the greater palatine canal"

U.S. patent application Ser. No. 11/465,381, filed Aug. 17, 2006, entitled, "Stimulation for treating brain events and other conditions"

U.S. patent application Ser. No. 11/668,305, filed Jan. 19, 2007, entitled, "Stimulation of the otic ganglion for treating medical conditions"

In an embodiment of the present invention, electrical stimulation system 20 comprises circuitry described in one or more of the above-mentioned applications.

In an embodiment of the present invention, an MTS is stimulated using the magnetic stimulation apparatus and methods described in the above-mentioned U.S. patent application Ser. No. 10/783,113.

As used in the present application and in the claims, the BBB comprises the tight junctions opposing the passage of most ions and large molecular weight compounds between the blood and brain tissue.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description. For example, elements which are shown in a figure to be housed within one integral unit may, for some applications, be disposed in a plurality of distinct units. Similarly, apparatus for communication and power transmission which are shown to be coupled in a wireless fashion may, alternatively, be coupled in a wired fashion, and apparatus for communication and power transmission which are shown to be coupled in a wired fashion may, alternatively, be coupled in a wireless fashion.

The invention claimed is:

1. A method comprising:

identifying that a subject is at particular future risk of suffering from vascular dementia (VaD) even though the subject displays no symptoms of VaD at the time of the identifying; and responding to the identifying by reducing a risk of development of the VaD by:

applying electrical stimulation to a site of the subject at least intermittently during a period having a duration of at least four weeks, the site selected from the group consisting of: a sphenopalatine ganglion (SPG), a greater palatine nerve, a lesser palatine nerve, a sphenopalatine nerve, a communicating branch between a maxillary nerve and an SPG, an otic ganglion, an afferent fiber going into the otic ganglion, an efferent fiber going out of the otic ganglion, an infraorbital nerve, a vidian nerve, a greater superficial petrosal nerve, and a lesser deep petrosal nerve, and configuring the stimulation applied to the site to induce at least one neuroprotective occurrence selected from the group consisting of: an increase in cerebral blood flow (CBF) of the subject, and a release of one or more neuroprotective substances.

2. The method according to claim 1, wherein identifying comprises identifying that the subject suffers from low cerebral blood perfusion.

3. The method according to claim 1, wherein identifying comprises identifying that the subject suffers from reduced cardiac output.

4. The method according to claim 1, wherein applying the stimulation comprises implanting an electrical stimulator in a vicinity of the site, and activating the stimulator to apply the stimulation.

5. The method according to claim 1, wherein the site includes the SPG, and wherein applying the stimulation comprises applying the stimulation to the SPG.

6. The method according to claim 1, wherein identifying comprises identifying that the subject has suffered from a stroke, and is thus at particular future risk of suffering from post-stroke dementia.

7. The method according to claim 6, wherein identifying comprises assessing an age of the subject at a time of the stroke.

8. The method according to claim 6, wherein identifying comprises assessing a severity of the stroke.

9. The method according to claim 6, wherein identifying comprises identifying that the subject suffers from hypertension.

10. The method according to claim 6, wherein identifying comprises assessing an indication of cognitive function of the subject during an acute stage of the stroke.

11. The method according to claim 1, wherein configuring the stimulation comprises setting a strength of the stimulation to be insufficient to induce a significant increase in permeability of a blood-brain barrier (BBB) of the subject.

12. The method according to claim 1, wherein the at least one neuroprotective occurrence includes the increase in the CBF, and wherein configuring comprises configuring the stimulation to induce the increase in the CBF.

13. The method according to claim 1, wherein applying the electrical stimulation comprises applying excitatory electrical stimulation to the site.

* * * * *